(12) United States Patent
Kim et al.

(10) Patent No.: US 9,615,879 B2
(45) Date of Patent: Apr. 11, 2017

(54) OPEN IRRIGATED ABLATION CATHETER WITH PROXIMAL COOLING

(71) Applicant: BOSTON SCIENTIFIC SCIMED, INC., Maple Grove, MN (US)

(72) Inventors: Isaac J. Kim, San Jose, CA (US); Mark D. Mirigian, San Jose, CA (US); Desmond Cheung, San Jose, CA (US); Simplicio A. Velilla, Santa Clara, CA (US); Robert Quintos, Newark, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 121 days.

(21) Appl. No.: 14/209,897

(22) Filed: Mar. 13, 2014

(65) Prior Publication Data
US 2014/0276759 A1    Sep. 18, 2014

Related U.S. Application Data

(60) Provisional application No. 61/793,649, filed on Mar. 15, 2013.

(51) Int. Cl.
| *A61B 18/12* | (2006.01) |
| *A61B 18/14* | (2006.01) |
| *A61M 25/00* | (2006.01) |
| *A61B 18/00* | (2006.01) |
| *A61B 17/00* | (2006.01) |

(52) U.S. Cl.
CPC ..... *A61B 18/1492* (2013.01); *A61B 2017/00039* (2013.01); *A61B 2017/00053* (2013.01); *A61B 2018/00029* (2013.01); *A61B 2018/00821* (2013.01); *A61B 2018/00839* (2013.01);
(Continued)

(58) Field of Classification Search
CPC ...... A61B 18/1492; A61B 2017/00039; A61B 2017/00053; A61B 2018/00029; A61B 2018/00821; A61B 2018/00839; A61B 2218/002; A61M 2025/0073; A61M 25/007
See application file for complete search history.

(56) References Cited

U.S. PATENT DOCUMENTS

| 4,636,313 A | 1/1987 | Vaillancourt |
| 5,238,004 A | 8/1993 | Sahatjian et al. |

(Continued)

FOREIGN PATENT DOCUMENTS

| CN | 102232869 A | 11/2011 |
| CN | 102232870 A | 11/2011 |

(Continued)

OTHER PUBLICATIONS

International Preliminary Report on Patentability issued in PCT/US2013/07346.1, mailed Jun. 18, 2015, 11 pages.

(Continued)

*Primary Examiner* — Daniel Fowler
(74) *Attorney, Agent, or Firm* — Faegre Baker Daniels LLP

(57) ABSTRACT

Medical devices and methods for using medical devices are disclosed. An example medical device may include an open-irrigated ablation catheter. The open-irrigated ablation catheter may include a catheter body, an electrode tip body with one or more irrigation ports at a distal end, and a proximal insert for providing cooling fluid to a proximal end of the electrode tip body.

18 Claims, 24 Drawing Sheets

(52) U.S. Cl.
CPC ...... *A61B 2218/002* (2013.01); *A61M 25/007* (2013.01); *A61M 2025/0073* (2013.01)

(56) References Cited

U.S. PATENT DOCUMENTS

| | | | |
|---|---|---|---|
| 5,413,107 A | 5/1995 | Oakley et al. | |
| 5,458,597 A * | 10/1995 | Edwards ................ | A61N 5/045 604/21 |
| 5,545,161 A | 8/1996 | Imran | |
| 5,584,872 A | 12/1996 | LaFontaine et al. | |
| 5,643,197 A | 7/1997 | Brucker et al. | |
| 5,688,267 A | 11/1997 | Panescu et al. | |
| 5,772,609 A | 6/1998 | Nguyen et al. | |
| 5,779,699 A | 7/1998 | Lipson | |
| 5,871,525 A | 2/1999 | Edwards et al. | |
| 5,895,355 A | 4/1999 | Schaer | |
| 5,932,035 A | 8/1999 | Koger et al. | |
| 6,013,052 A | 1/2000 | Durman et al. | |
| 6,053,912 A | 4/2000 | Panescu et al. | |
| 6,120,476 A | 9/2000 | Fung et al. | |
| 6,139,510 A | 10/2000 | Palermo et al. | |
| 6,287,301 B1 | 9/2001 | Thompson et al. | |
| 6,508,803 B1 | 1/2003 | Horikawa et al. | |
| 7,628,788 B2 | 12/2009 | Datta | |
| 7,914,528 B2 | 3/2011 | Wang et al. | |
| 8,128,620 B2 | 3/2012 | Wang et al. | |
| 8,273,082 B2 * | 9/2012 | Wang ................ | A61B 18/1492 604/247 |
| 8,517,999 B2 | 8/2013 | Pappone et al. | |
| 2003/0004506 A1 | 1/2003 | Messing | |
| 2003/0009094 A1 | 1/2003 | Segner et al. | |
| 2005/0203410 A1 | 9/2005 | Jenkins | |
| 2006/0074444 A1 | 4/2006 | Lin et al. | |
| 2006/0184165 A1 | 8/2006 | Webster et al. | |
| 2007/0270791 A1 | 11/2007 | Wang et al. | |
| 2008/0071267 A1 | 3/2008 | Wang et al. | |
| 2008/0091193 A1 | 4/2008 | Kauphusman et al. | |
| 2008/0147060 A1 | 6/2008 | Choi | |
| 2008/0161789 A1 | 7/2008 | Thao et al. | |
| 2008/0161792 A1 | 7/2008 | Wang et al. | |
| 2008/0161795 A1 | 7/2008 | Wang et al. | |
| 2008/0200801 A1 | 8/2008 | Wildes et al. | |
| 2008/0243214 A1 | 10/2008 | Koblish | |
| 2008/0249522 A1 | 10/2008 | Pappone et al. | |
| 2009/0012517 A1 | 1/2009 | de la Rama et al. | |
| 2009/0093810 A1 | 4/2009 | Subramaniam et al. | |
| 2009/0093811 A1 | 4/2009 | Koblish et al. | |
| 2009/0125016 A1 | 5/2009 | Wang et al. | |
| 2009/0143779 A1 | 6/2009 | Wang et al. | |
| 2009/0163913 A1 | 6/2009 | Wang et al. | |
| 2009/0171345 A1 | 7/2009 | Miller et al. | |
| 2009/0177193 A1 | 7/2009 | Wang et al. | |
| 2009/0259222 A1 | 10/2009 | Wang et al. | |
| 2010/0114093 A1 | 5/2010 | Mahapatra et al. | |
| 2010/0168728 A1 | 7/2010 | Wang et al. | |
| 2010/0249601 A1 | 9/2010 | Courtney | |
| 2010/0331658 A1 | 12/2010 | Kim et al. | |
| 2011/0009857 A1 | 1/2011 | Subramaniam et al. | |
| 2011/0022041 A1 | 1/2011 | Ingle et al. | |
| 2011/0092969 A1 | 4/2011 | Wang et al. | |
| 2011/0144657 A1 | 6/2011 | Fish et al. | |
| 2011/0201973 A1 | 8/2011 | Stephens et al. | |
| 2011/0224667 A1 | 9/2011 | Koblish et al. | |
| 2011/0257523 A1 | 10/2011 | Hastings et al. | |
| 2011/0264089 A1 | 10/2011 | Zirkle et al. | |
| 2011/0270046 A1 | 11/2011 | Paul et al. | |
| 2011/0270246 A1 | 11/2011 | Clark et al. | |
| 2012/0017287 A1 | 1/2012 | Bumiller et al. | |
| 2012/0029504 A1 | 2/2012 | Afonso et al. | |
| 2012/0029511 A1 | 2/2012 | Smith et al. | |
| 2012/0035466 A1 | 2/2012 | Tegg | |
| 2012/0035539 A1 | 2/2012 | Tegg | |
| 2012/0035605 A1 | 2/2012 | Tegg et al. | |
| 2012/0046610 A1 | 2/2012 | Rankin | |
| 2012/0130363 A1 | 5/2012 | Kim et al. | |
| 2012/0150175 A1 | 6/2012 | Wang et al. | |
| 2012/0165812 A1 | 6/2012 | Christian | |
| 2012/0172871 A1 | 7/2012 | Hastings et al. | |
| 2012/0221001 A1 | 8/2012 | Tegg et al. | |
| 2013/0137980 A1 | 5/2013 | Waters et al. | |
| 2014/0187893 A1 | 7/2014 | Clark et al. | |
| 2014/0276759 A1 | 9/2014 | Kim et al. | |

FOREIGN PATENT DOCUMENTS

| | | |
|---|---|---|
| EP | 1690510 A1 | 8/2006 |
| EP | 2380519 A1 | 10/2011 |
| JP | H11505747 A | 5/1999 |
| JP | 2011500156 A | 1/2011 |
| JP | 2011229918 A | 11/2011 |
| JP | 2012531967 A | 12/2012 |
| JP | 2012532737 A | 12/2012 |
| JP | 2014128674 A | 7/2014 |
| WO | 2009048824 A1 | 4/2009 |
| WO | 2009048943 A1 | 4/2009 |
| WO | 2014151876 A1 | 9/2014 |

OTHER PUBLICATIONS

International Preliminary Report on Patentabiiity issued in PCT/US2014/026509, mailed Sep. 24, 2015, 12 pages.
International Preliminary Report on Patentabiiity issued in PCT/US2014/026602, mailed Sep. 24, 2015, 10 pages.
International Search Report and Written Opinion issued in PCT/US2013/073461, mailed Jun. 6, 2014, 15 pages.
International Search Report and Written Opinion issued in PCT/US2014/026509, mailed Nov. 11, 2014, 16 pages.
International Search Report and Written Opinion issued in PCT/US2014/026602, mailed Jun. 25, 2014, 12 pages.

* cited by examiner

OPEN IRRIGATED ABLATION CATHETER WITH PROXIMAL COOLING

CROSS-REFERENCE TO RELATED APPLICATIONS

This application claims priority under 35 U.S.C. §119 to U.S. Provisional Application Ser. No. 61/793,649, filed Mar. 15, 2013, the entirety of which is incorporated herein by reference.

TECHNICAL FIELD

The present disclosure pertains to medical devices. More particularly, the present disclosure pertains to systems, devices and methods related to open-irrigated catheters used to perform ablation functions.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias. Ablation is one way of treating arrhythmias and restoring normal contraction. The sources of the aberrant pathways (called focal arrhythmia substrates) are located or mapped using mapping electrodes situated in a desired location. After mapping, the physician may ablate the aberrant tissue. In radio frequency (RF) ablation, RF energy is directed from the ablation electrode through tissue to an electrode to ablate the tissue and form a lesion.

Heat is generated during the RF ablation process, and this heat may cause a thrombus (blood clot). Some ablation catheter systems have been designed to cool the electrode and surrounding tissue. Alternative or new designs or methods for cooling the electrode and/or surrounding tissue are desirable.

BRIEF SUMMARY

This disclosure provides design, materials, methods of making, and use alternatives for medical devices. For example, some embodiments related to open-irrigated catheter systems that pump a cooling fluid, such as a saline solution, through a lumen in the body of the catheter, out through the ablation electrode, and into surrounding tissue. The cooling fluid cools the ablation electrode and surrounding tissue, thus reducing the likelihood of a thrombus, preventing or reducing impedance rise of tissue in contact with the electrode tip, and increasing energy transfer to the tissue because of the lower tissue impedance.

An example medical device may include an open-irrigated ablation catheter system. The open-irrigated catheter system may include a catheter body, an electrode tip body, a proximal insert, and a fluid diverting member. The electrode tip body may have a distal end and a proximal end configured for connection to the catheter body. The electrode tip body may have a wall defining an open interior region, and the wall may have one or more irrigation port in fluid communication with the open interior region. The wall may be conductive for delivering radio frequency (RF) energy. The proximal insert may be positioned at least partially within the proximal end of the electrode tip body, and may define at least one lumen extending therethrough. The fluid diverting member may be spaced from a distal end of the lumen and may extend across at least a portion of the lumen such that at least a portion of fluid flowing distally through the lumen impacts the fluid diverting member and is diverted towards the wall before flowing into the interior region and out through the one or more irrigation port.

The open-irrigated catheter system may further include a distal insert positioned within the electrode tip body that separates the open interior region into a distal fluid chamber and a proximal fluid chamber. The distal insert may have an opening fluidly connecting the distal and proximal fluid chambers such that at least one irrigation port is in fluid communication with the distal fluid chamber.

Another example ablation catheter system may include a catheter body including a proximal portion and a distal portion defining a distal end and a lumen extending therethrough, and an electrode tip body having a wall defining an open interior region. The body may include a proximal portion including an open proximal end, and the proximal portion may include one or more openings extending through the wall. The proximal portion of the electrode tip body may be disposed within the lumen at the distal end of the catheter body such that the distal end of the catheter body extends distally of the one or more openings through the wall of the electrode tip body.

Another example open-irrigated ablation catheter system may include a catheter body, an electrode tip body, and a proximal insert. The electrode tip body may have a proximal end configured for connection to the catheter body, the electrode tip body having a wall defining an open interior region and including a main body portion and a proximal portion. The main body portion may have one or more irrigation port in fluid communication with the open interior region, and the proximal portion may have one or more openings through the wall, wherein the wall is conductive for delivering radio frequency (RF) energy. The proximal insert may be positioned at least partially within the proximal end of the electrode tip body, and may include a proximal lip and a main body portion. The main body portion may have a diameter less than a diameter of the proximal lip, and may include at least one lumen extending therethrough. The proximal insert may include one or more openings through a sidewall in the main body portion in fluid communication with the at least one lumen. The main body portion of the proximal insert may be sized to be mounted within the proximal portion of the electrode tip body with the proximal lip extending radially beyond the electrode tip body, substantially aligning the openings in the proximal insert and the openings in the proximal portion of the electrode tip body. The proximal lip may be sized to engage an inner surface of a distal portion of the catheter body and define a space between an outer surface of the proximal portion of the electrode tip body and the inner surface of the catheter body such that a portion of cooling fluid flowing through the at least one lumen passes through the openings in the proximal insert and the openings in the proximal portion of the electrode tip body and into the space between the catheter body and the electrode tip body, thereby cooling a region where the catheter body joins the electrode tip body.

The catheter system may further include a crown element configured to fit over the proximal end of the electrode tip body. The crown element may have one or more spaced apart legs configured to be disposed between the openings through the wall of the proximal portion of the electrode tip body, the crown directing fluid flow from the openings in the proximal portion toward the distal end of the catheter body.

The catheter system may further include a fluid diverting member spaced from a distal end of a fluid lumen extending through the catheter, the fluid diverting member extending across at least a portion of the lumen such that at least a portion of fluid flowing distally through the lumen impacts the fluid diverting member and is diverted towards the wall of the electrode tip body before flowing into the interior region and out through the irrigation ports.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
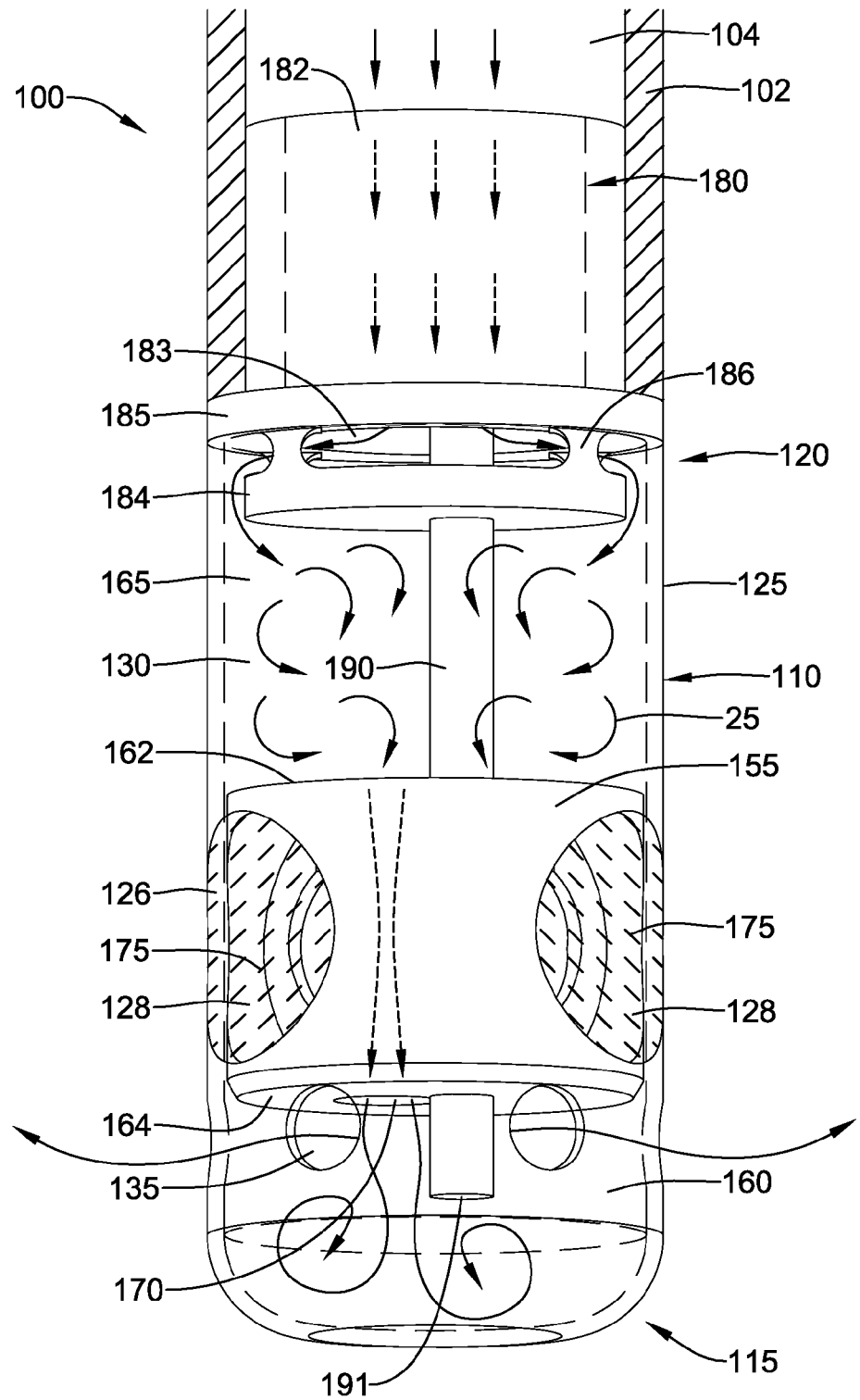
FIG. 1 is a perspective view of the distal end of an open-irrigated catheter according to an embodiment of the present subject matter.
Figure 2:
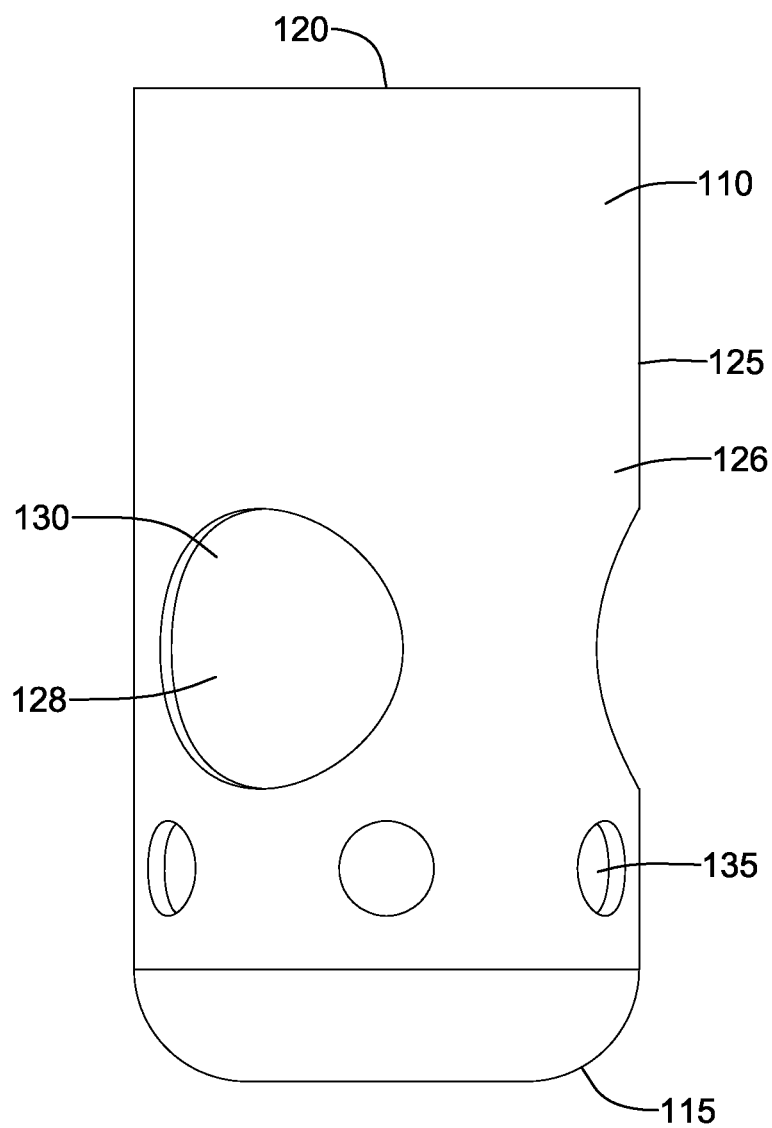
FIG. 2 is a perspective view of the electrode tip body of FIG. 1.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

This present subject matter generally relates to an open-irrigated radiofrequency (RF) ablation catheter system. In some embodiments, the catheter may be referred to as a hybrid catheter as it can be used simultaneously for both localized mapping and ablation functions. However, not all embodiments would necessarily include both the mapping and ablation functions, and may instead incorporate only one or the other function. The hybrid catheter is configured to provide localized, high resolution ECG signals during ablation. The localized mapping enables the mapping to be more precise than that which can be achieved with conventional ablation catheters. The hybrid catheter has an open-irrigated catheter design. A cooling fluid, such as a saline, is delivered through the catheter to the catheter tip, where the fluid exits through irrigation ports to cool the electrode and surrounding tissue. Clinical benefits of such a catheter include, but are not limited to, controlling the temperature and reducing coagulum formation on the tip of the catheter, preventing impedance rise of tissue in contact with the catheter tip, and maximizing potential energy transfer to the tissue. Additionally, the localized intra cardiac electrical activity can be recorded in real time or near-real time right at the point of energy delivery.

The some embodiments may be used within body lumens, chambers or cavities for diagnostic or therapeutic purposes in those instances where access to interior bodily regions is obtained through, for example, the vascular system or alimentary canal and/or with minimally invasive surgical procedures. For example, some embodiments have application in the diagnosis and treatment of arrhythmia conditions within the heart. Some embodiments also have application in the diagnosis or treatment of ailments of the gastrointestinal tract, prostrate, brain, gall bladder, uterus, and other regions of the body. With regard to the treatment of conditions involving the heart, some embodiments can be used to create lesions to treat atrial fibrillation, atrial flutter and ventricular tachycardia. Additionally, some embodiments can be used to modulate, block, or ablate nerve bodies in the treatment of neural structures. For example, some embodiments have application in the treatment of congestive heart failure, hypertension, and other cardio-renal diseases. With regard to the treatment of cardio-renal diseases, some embodiments can be used to modulate neural function of the renal nerve.

If near laminar flow conditions are at the exit ports of an open-irrigated catheter, stable eddy currents may be formed around the electrode. Under these conditions, there could be hot spots by the ablation electrode, particularly around the proximal part of the electrode. If these stable eddy currents trap blood platelets near the electrode, and if these trapped platelets are activated due to heat and shear force, a thrombus could potentially form. Near laminar flow of cooling fluid from the irrigation ports tends to cause the cooling fluid to flow away from the ablation electrode and the tissue near the ablation site, potentially causing uneven cooling and localized hot spots along the ablation electrode.

The present subject matter provides systems and methods for cooling the ablation electrode and the surrounding tissue in a more uniform manner. An open-irrigated RF ablation catheter is designed to divert the initial flow of cooling fluid within the electrode to improve the uniformity of cooling. The risk of thrombus formation significantly decreases using diverted flow of cooling fluid to uniformly cool the electrode. Although the present embodiments are not so limited, the exemplary catheter is configured for use within the heart and, accordingly, is about 5 French to about 11 French (about 1.67 mm to about 3.67 mm) in diameter. The wall thickness of the exemplary electrode tip body may be about 0.05 mm to about 0.3 mm. The portion of the catheter that is inserted into the patient is typically from about 60 to 160 cm in length. The length and flexibility of the catheter allow the catheter to be inserted into a main vein or artery (typically the femoral vein), directed into the interior of the heart, and then manipulated such that the desired electrode (s) contact the target tissue. Fluoroscopic imaging may be used to provide the physician with a visual indication of the location of the catheter.

Referring now to FIGS. 1-4B, which show various components of an example open irrigated catheter system 100, FIG. 1 illustrates the distal end of an open irrigated catheter system 100 including a catheter shaft 102 with a lumen 104, an electrode tip body 110, a proximal insert 180, a distal insert 155, and a thermocouple 190. The electrode tip body 110 is generally hollow with a closed distal end 115, an open interior region 130, and an open proximal end 120. In the illustrated embodiment, the hollow electrode tip body 110 has a generally cylindrical shape. The electrode tip body 110 may include one or more openings or irrigation ports 135 and one or more openings 128 for receiving electrodes such as mapping electrodes.

Figure 3:
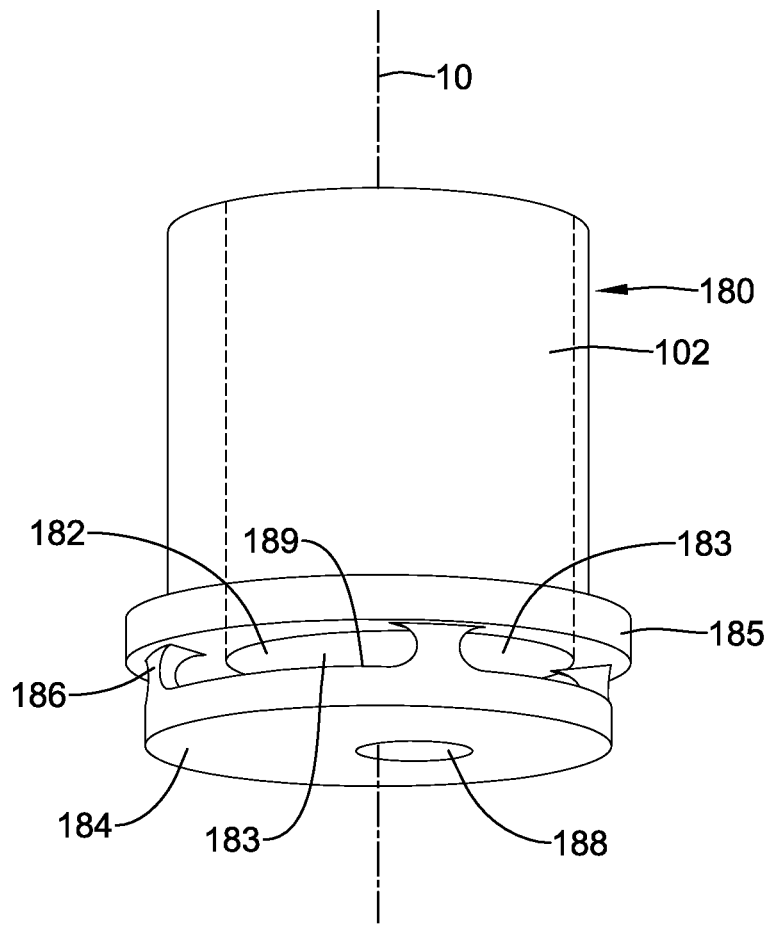
FIG. 3 is a perspective view of the proximal insert of FIG. 1.
Figure 4A:
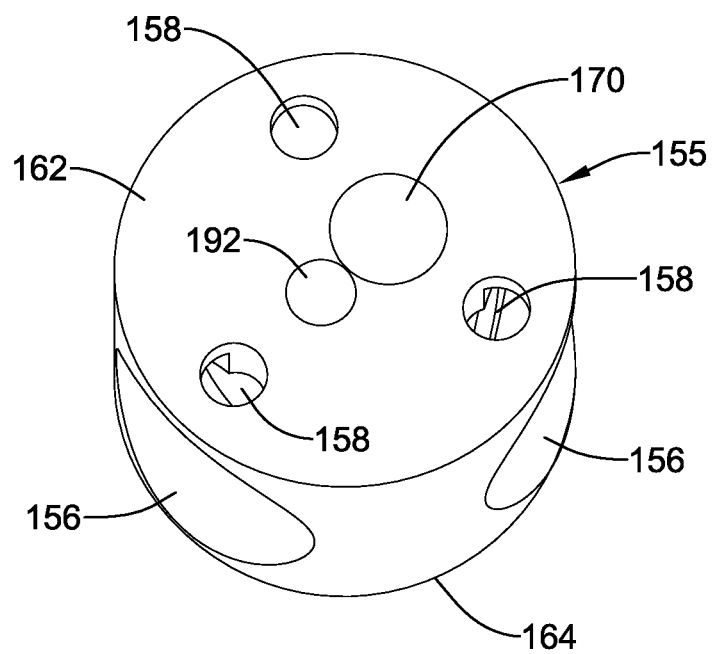
FIG. 4A is a top perspective view of the distal insert of FIG. 1.
Figure 4B:
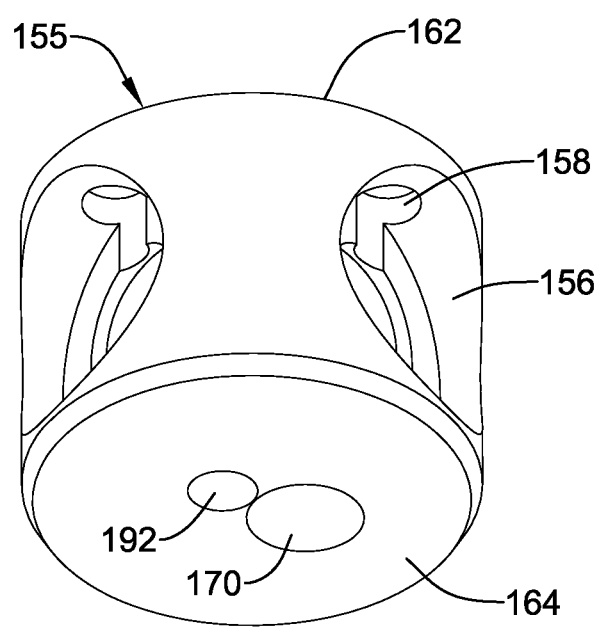
FIG. 4B is a bottom perspective view of the distal insert of FIG. 1.

A proximal insert 180 fits into the open proximal end 120 of the electrode tip body 110. The proximal insert 180 includes a lumen 182 extending longitudinally therethrough. A lip 185 may extend radially out from the main body of the proximal insert 180, as illustrated in FIG. 3. The lip 185 is sized to fit into the open proximal end 120 of the electrode tip body 110. In some embodiments, a reduced circumference of the proximal insert proximal of the lip 185 provides a region for connecting the electrode tip body 110 to the distal end of a catheter shaft 102. In other embodiments, the proximal insert 180 may have a substantially uniform exterior dimension without a lip. The proximal insert 180 may have any shape and dimension provided at least a portion of the proximal insert fits within the open proximal end 120 of the electrode tip body 110.

Cooling fluid can be delivered through the lumen 104 of the catheter shaft 102, through the lumen 182 of the proximal insert 180 and into the open interior region 130 of the electrode tip 110. A fluid diverting member such as a plate 184 is designed to cause the cooling fluid to be diverted towards the wall 125 at the proximal end 120 of the electrode tip body 110, where hot spots may otherwise develop. The plate 184 is spaced from the distal end of the proximal insert 180 and may be attached to the proximal insert 180 with one or more legs 186 or other structure. Alternatively, the plate 184 may be attached to the wall 125 of the electrode tip body 110 with one or more legs such that openings allow fluid to pass from the distal end 183 of the lumen 182 into the open interior region 130 of the electrode tip body 110. The plate 184 may extend transverse to the longitudinal axis 10 of the proximal insert 180. In other embodiments the upper surface of the plate 184 may be angled or canted relative to the longitudinal axis 10. The plate 184 may cover the distal end 183 of the lumen 182, such that fluid flowing distally through the lumen 182 impacts the plate 184 and is redirected towards the wall 125 of the electrode tip body 110.

The redirected flow of cooling fluid provides cooling of the proximal end 120 of the electrode tip body 110 as the fluid flows across the plate 184 and between the plate 184 and wall 125 into the open interior region 130 of the electrode tip body 110. The plate 184 may have an opening 188 for receiving the thermocouple 190. The plate 184 may have a shape generally matching the shape of the electrode tip body. For example, the electrode tip body 110 may be generally cylindrical and the plate may be circular. In other embodiments, the plate may have a different shape than the electrode tip body. For example, the electrode tip body may be cylindrical and the plate may be square, octagonal, oval, or have any other shape. The plate may be sized to extend beyond the outer edge of the lumen 182 but not to the electrode tip wall 125. The distance between the edge of the plate 184 and the electrode tip wall 125 may be selected to achieve a desired amount of circulating cooling fluid proximal of the plate 184, near the distal end of the catheter body and the proximal end of the electrode tip body. In some embodiments, the plate may have one or more openings (not shown) to allow fluid to flow through the plate as well as around it. The plate 184 may extend to the wall 125 of the electrode tip body when openings are present in the plate. The plate 184 may have any thickness and may have a flat proximal surface 189 or may have surface irregularities and/or angles that further disrupt fluid flow. For example, the plate may have a wavy, ridged, and/or grooved proximal surface, and/or the plate may have protrusions and/or indentations on the proximal surface (not shown). The distal surface of the plate may have the same surface characteristics as the proximal surface or the two surfaces may have different surface characteristics.

A distal insert 155 divides the open interior region 130 of the electrode tip body 110 into a distal fluid reservoir 160 and a proximal fluid reservoir 165, each of which act as cooling chambers. The distal insert 155 may be a thermal mass. The distal insert 155 has an opening 170 extending from a proximal surface 162 of the distal insert to a distal surface 164. The opening 170 fluidly connects the distal fluid reservoir 160 and the proximal fluid reservoir 165, allowing cooling fluid to flow therethrough. One or more irrigation ports 135 through the wall 125 of the electrode tip body 110 near the distal end 115 allows cooling fluid to exit the device and cool the tip and surrounding tissues. If more than one irrigation port is present, the irrigation ports 135 may be equally spaced around the circumference of the electrode tip body. However, the present subject matter is not limited to equally-spaced irrigation ports or to a particular number of irrigation ports. The system can be designed with other numbers and arrangements of irrigation ports. The catheter system may include a temperature sensor mounted within the electrode tip body 110. In the illustrated embodiment, the temperature sensor is a thermocouple 190 that extends through the proximal insert 180, through an opening 188 in the plate 184, and through an opening 192 in the distal insert 155, allowing a distal end 191 of the thermocouple to be positioned in the distal fluid reservoir 160.

The cooling fluid cools both the electrode tip body 110 and the tissue adjacent to the perimeter of the electrode tip body. For example, the cooling fluid draws heat from the electrode tip body 110 (including the thermal mass distal insert 155) and reduces the temperature of the electrode. The presence of the plate 184, the proximal fluid reservoir 165, the distal insert 155, and distal fluid reservoir 160 augments the fluid cooling because the fluid flows along the wall 125 and into the proximal fluid reservoir 165 where it circulates prior to entering the distal fluid reservoir 160, where the fluid again circulates prior to exiting the electrode tip body 110 by way of the irrigation ports 135. The decrease in electrode and tissue temperature reduces the likelihood that the tissue in contact with the electrode tip body 110 will char and/or that coagulum will form on the surface of the electrode tip body. As such, the amount of energy supplied to the tissue may be increased, and the energy is transferred to the tissue more efficiently, as compared to an electrode that is not configured for fluid cooling. This results in the formation of larger and deeper lesions. In addition to cooling tissue adjacent to the electrode tip body 110, fluid that exits the electrode tip body sweeps biological material such as blood and tissue away from the electrode, further reducing the likelihood of coagulum formation.

The plate 184, the proximal and distal fluid reservoirs 165, 160, respectively, the opening 170 in the distal insert, and the irrigation ports 135 are designed with appropriate dimensions and geometry with respect to each other to encourage turbulent fluid flow when pressurized cooling fluid flows out of the catheter body, through the proximal insert lumen 182, through the proximal fluid reservoir 165, through the opening 170 in the distal insert, through the distal fluid reservoir 160, and out the irrigation ports 135. Coolant is pumped at high pressure through the catheter. The plate 184 interrupts laminar flow, redirecting flow towards the wall 125 of the electrode tip body, where the fluid cools the proximal end 120 of the electrode tip body, mitigating overheating (edge effect). Fluid then flows around the plate 184 and into the proximal fluid reservoir 165, where the fluid circulates to cool the proximal portion of the electrode tip body distal of the plate 184. Laminar flow is further disturbed as the coolant is forced through opening 170 into the distal fluid reservoir 160. The turbulence increases as the coolant exits through the irrigation ports 135.

The edges of the irrigation ports may be purposely left rough and ragged. The distal end 115 of the electrode tip body is a relatively flat wall. The combination of these factors causes the fluid exiting the irrigation ports to create turbulence around the entire electrode body, encouraging a more uniform cooling of the electrode body and the dilution of the blood in the vicinity of the ablation electrode. Additionally, the arrangement of the irrigation ports with respect to the distal fluid reservoir encourages the fluid to flow out at an angle toward the proximal end of the ablation electrode to cause the cooling fluid to flow, in a turbulent manner, at the proximal end of the electrode as well as at the distal end of the electrode.

The catheter system 100 may include one or more mapping electrodes 175 shown in phantom in the drawings. The distal insert 155 illustrated in FIGS. 1, 4A and 4B includes openings or apertures 156 sized to receive a mapping electrode 175. The electrode tip wall 125 has a corresponding opening 128 in an exterior surface 126 thereof. In one embodiment, the device includes three mapping electrodes 175 spaced equidistant around the electrode. Four our more mapping electrodes may also be used. These microelectrodes may be used in the mapping function to image localized intra cardiac activity. The device may be used to record high resolution, precise localized electrical activity, to prevent excessive heating of the ablation electrode, to allow greater delivery of power, to prevent the formation of coagulum and to provide the ability to diagnose complex ECG activity. The proximal surface 162 of the distal insert 155 may also include openings 158 sized to receive electrical conductors (not shown) used to provide electrical connections to the mapping electrodes 175. The electrical conductors for the mapping electrodes, the electrode tip body 110 and the thermocouple 190 are incorporated into the catheter construction as is generally known in the art. By way of example and not limitation, an embodiment of the distal insert is fabricated from stainless steel. Additional details concerning mapping electrodes may be found in, for example, U.S. Publication. Nos. 2008/0243214 and 2010/0331658, which are hereby incorporated by reference.

Figure 5:
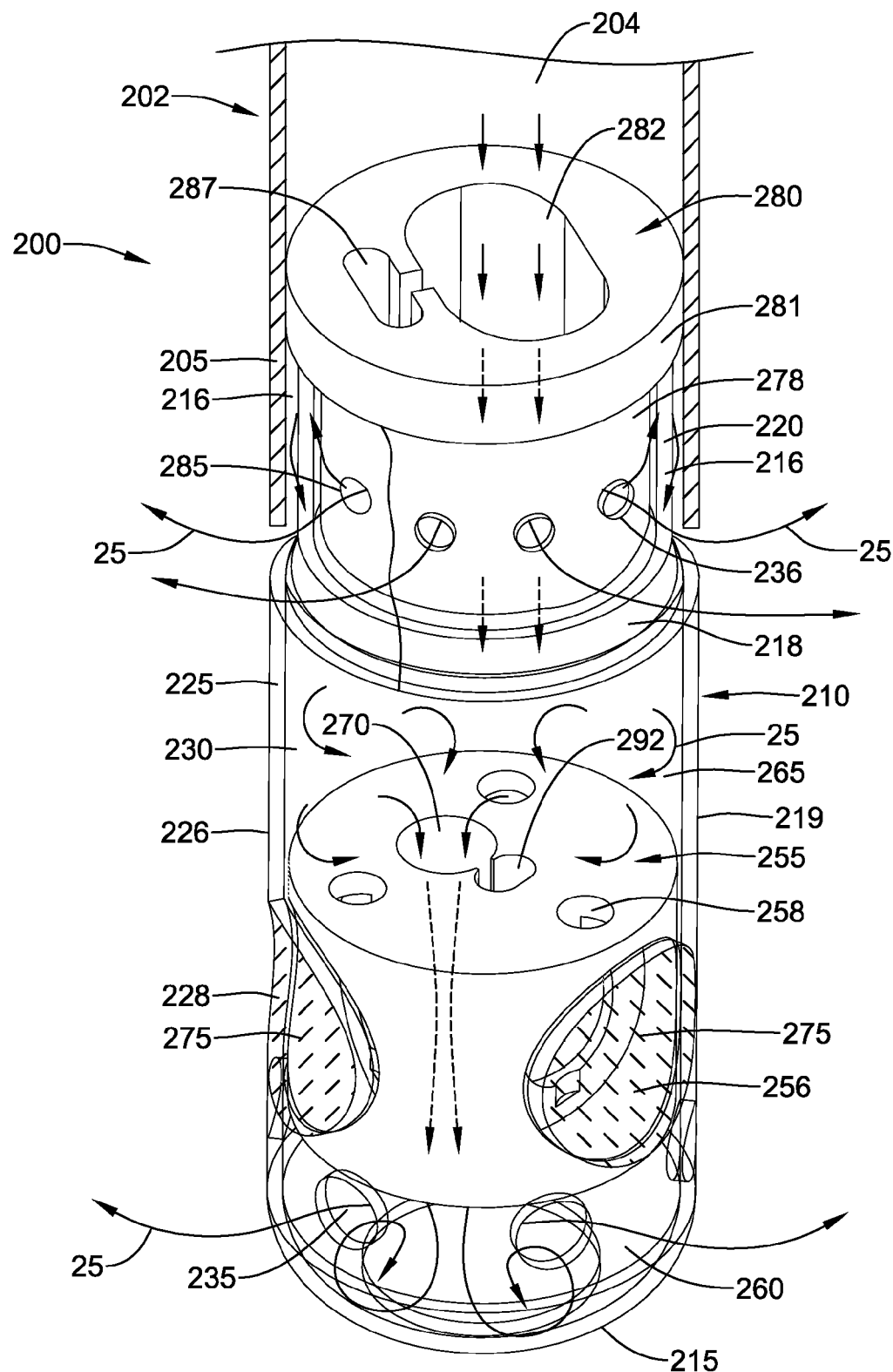
FIG. 5 is a perspective view of an open-irrigated catheter according to another embodiment of the present subject matter.
Figure 6A:
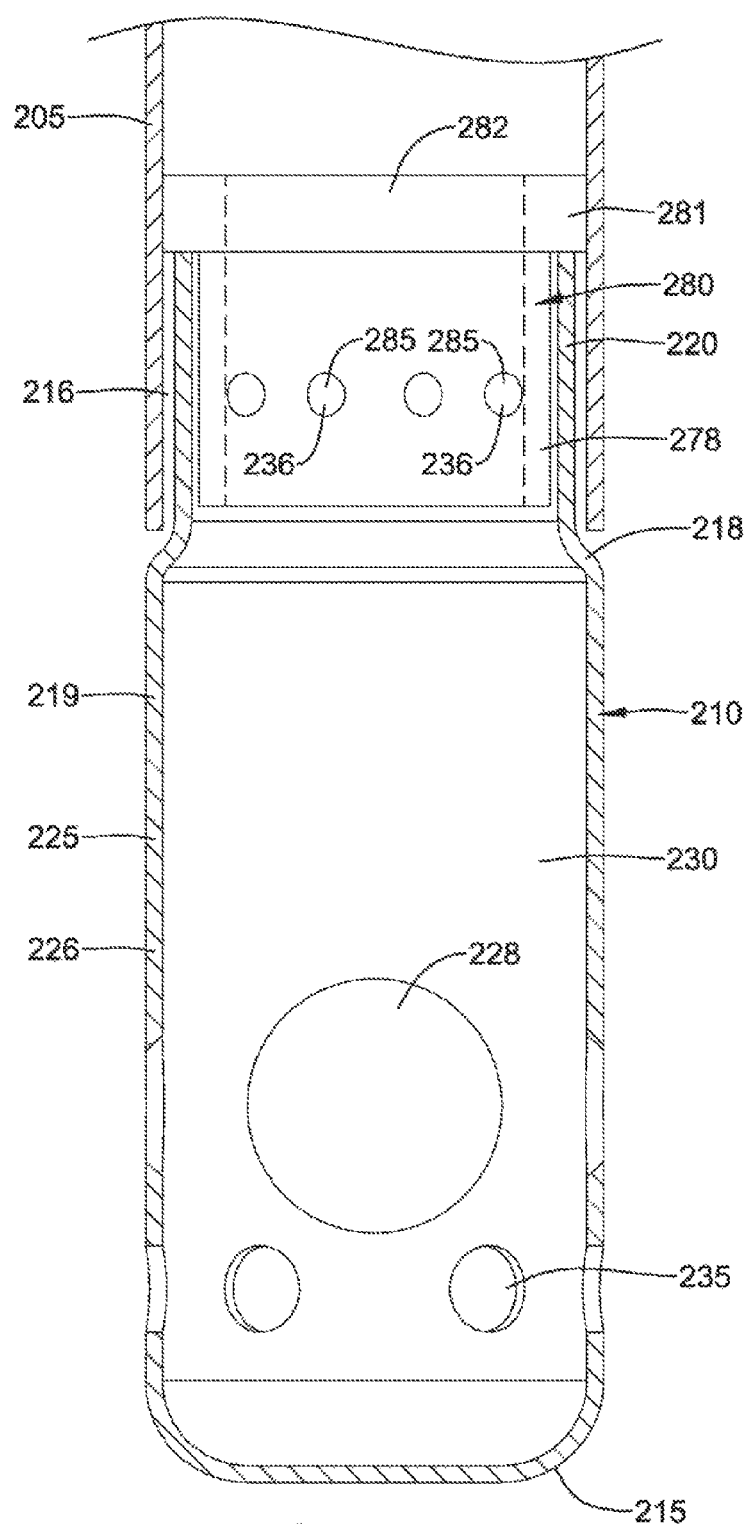
FIG. 6A is a side cross-sectional view of the electrode tip body and proximal insert of FIG. 5.
Figure 6B:
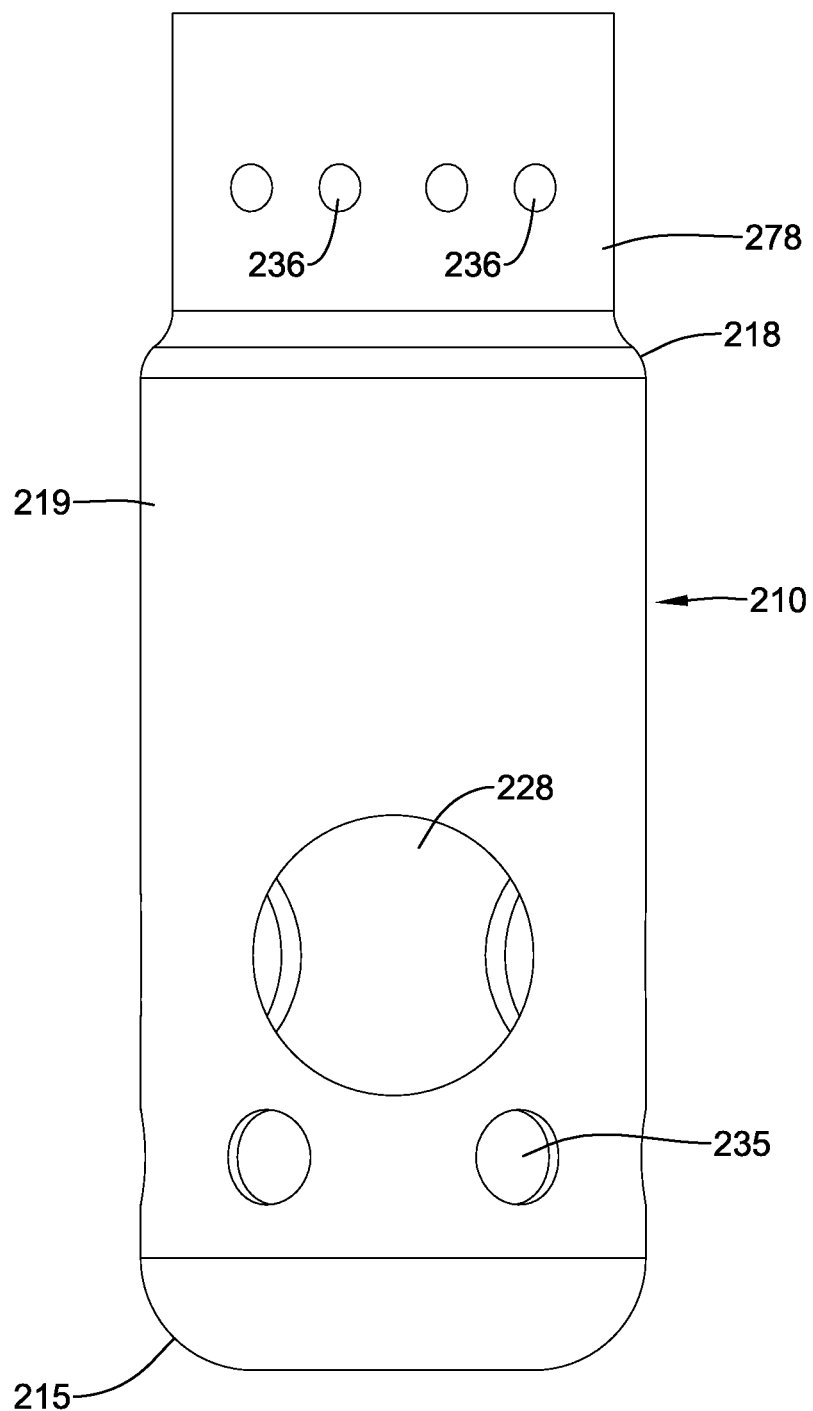
FIG. 6B is a perspective view of the electrode tip body of FIG. 5.

Another embodiment of electrode tip system 200 is illustrated in FIGS. 5-8B. Referring now to FIG. 5, which shows an electrode tip body 210 in perspective, and a catheter distal end 205 in cross section. The distal end of the open-irrigated catheter system 200 includes an electrode tip body 210, a proximal insert 280, a distal insert 255, and a catheter shaft 202 having a lumen 204 and a distal end 205. The electrode tip body 210 is generally hollow with a closed distal end 215, an open interior region 230, an open proximal end 220 and a main body 219. FIG. 6A shows a cross-section side view of the tip body 210, the distal end 205 of the catheter shaft 202, and the proximal insert 280. The distal insert 255 is not shown. FIG. 6B shows a perspective view of electrode tip body 210. As seen in FIGS. 6A and 6B, the hollow electrode tip body 210 has a generally cylindrical shape with a planar distal end 215. The electrode tip body 210 may have a shoulder region 218 joining a smaller diameter proximal end 220 to the main body 219. The diameter of the main body 219 may be sized to correspond to a diameter of the distal end 205 of the catheter shaft 202.

Figure 7A:
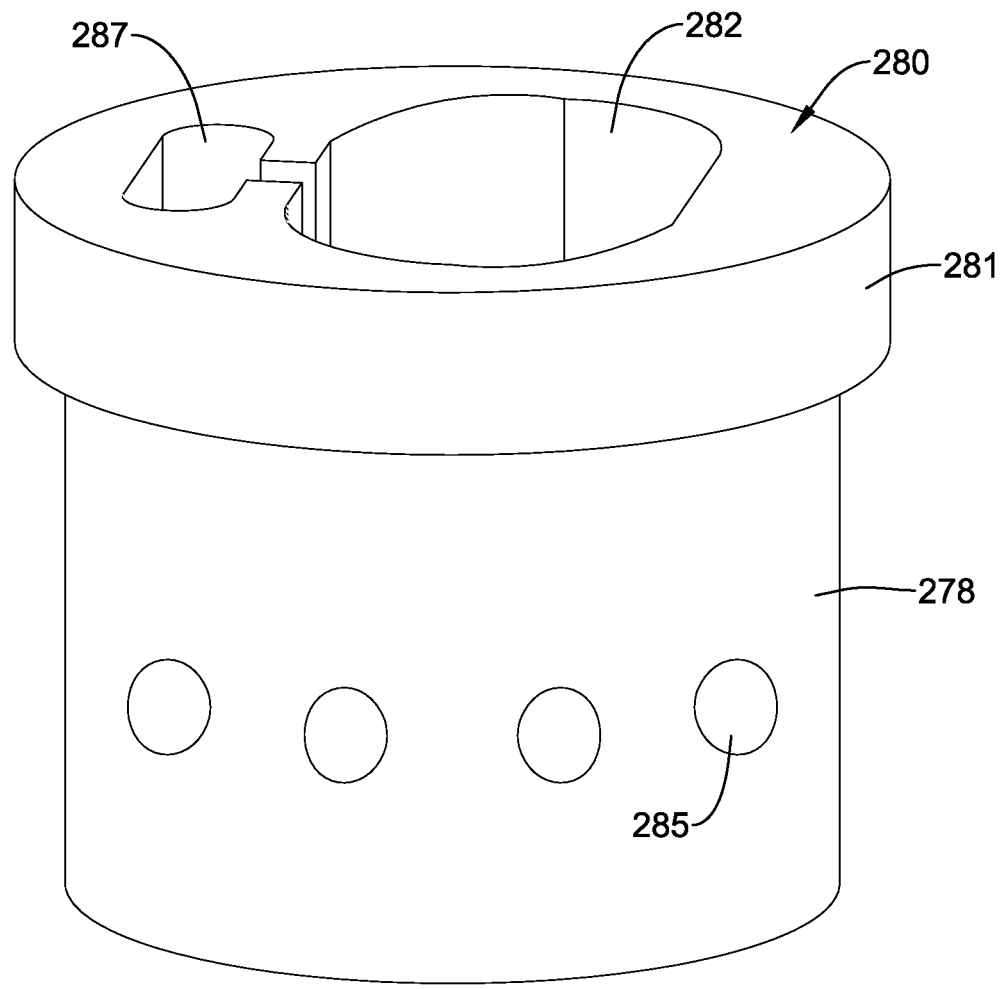
FIG. 7A is a top perspective view of the proximal insert of FIG. 5.
Figure 7B:
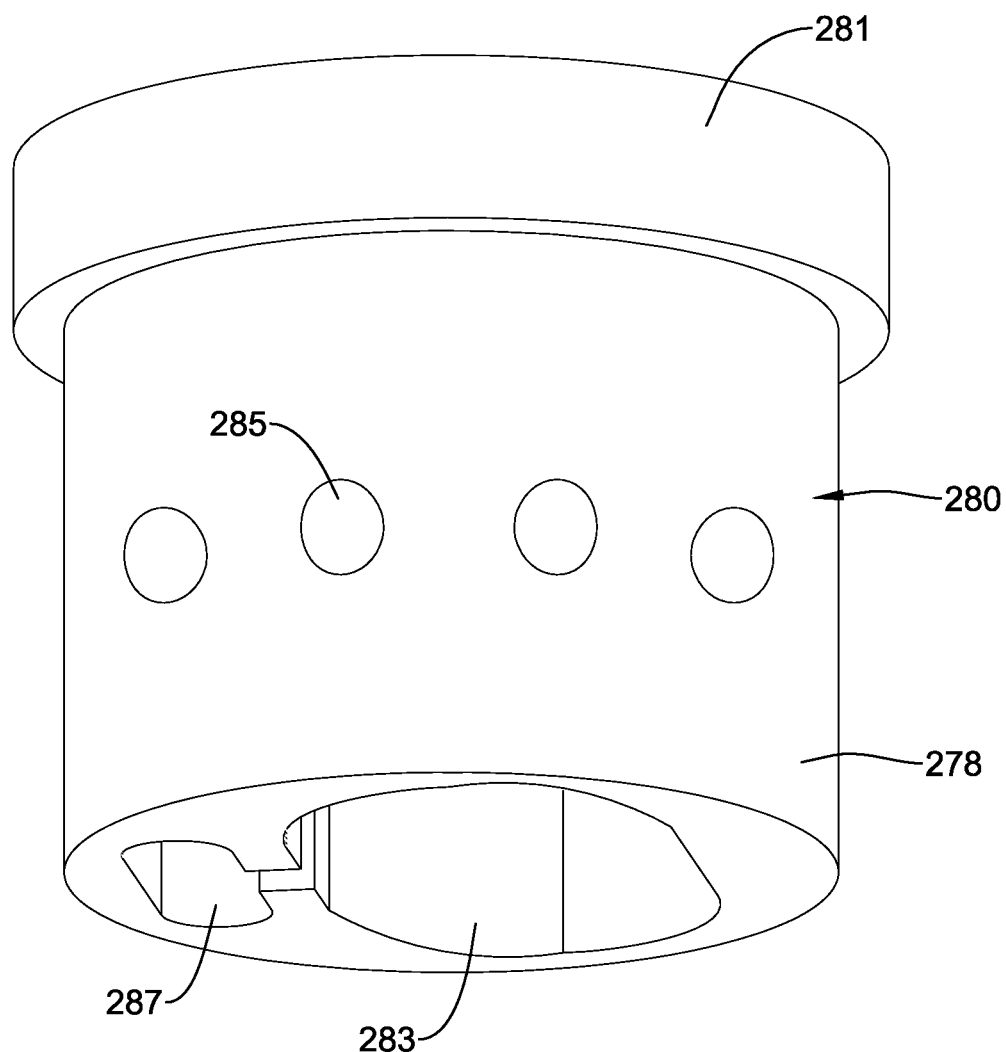
FIG. 7B is a bottom perspective view of the proximal insert of FIG. 5.

The electrode tip body 210 may include one or more irrigation ports 235 through the wall 225 of the electrode tip body 210 near the distal end 215. When more than one irrigation port is present, the irrigation ports 135 may be equally spaced around the circumference of the electrode tip body. However, the present subject matter is not limited to equally-spaced irrigation ports or to a particular number of irrigation ports. The system can be designed with other numbers and arrangements of irrigation ports. The electrode tip body 210 may also include one or more openings 228 for receiving electrodes such as mapping electrodes. The proximal end 220 of the electrode tip body 210 may have one or more openings 236 through the wall that allow cooling fluid to exit and cool the proximal region of the electrode tip body. If a plurality of openings are present, the openings 236 may be equally spaced around the circumference of the electrode tip body. However, the present subject matter is not limited to equally-spaced irrigation ports or to a particular number or arrangement of openings. A proximal insert 280 fits into the open proximal end 220 of the electrode tip body 210. The proximal insert 280 includes at least one fluid lumen 282 and a thermocouple opening 287 extending longitudinally therethrough. A proximal lip 281 extends radially out from the main body 278 of the proximal insert 280, as illustrated in FIGS. 5, 7A and 7B. The main body 278 is sized to fit into the open proximal end 220 of the electrode tip body 210 with the proximal lip 281 resting on and extending radially away from the proximal edge of the electrode tip body. The proximal lip 281 fits within the distal end 205 of the catheter shaft 202. The proximal lip 281 extending radially beyond the electrode tip body defines a space 216 between the proximal end 220 of the electrode tip body 210 and the catheter shaft 202. The proximal insert 280 may include openings 285 in the main body 278 allowing some cooling fluid to exit the lumen 282 and pass through openings 236 in the proximal end 220 of the electrode tip body 210. The openings 285 and 236 may be sized, numbered, and arranged to overlap, as illustrated in the cut-away region shown in FIG. 5 and in the cross-sectional view shown in FIG. 6A, or they may differ in any or all of size, number, and arrangement such that the openings 285 and 236 are offset. Cooling fluid, as shown by the fluid flow lines 25 in FIG. 5, exiting the openings 285 and 236 may circulate in the space 216 before exiting the device through a gap between the distal end 205 of the catheter shaft 202 and the shoulder region 218 of the electrode tip body 210.

Figure 8A:
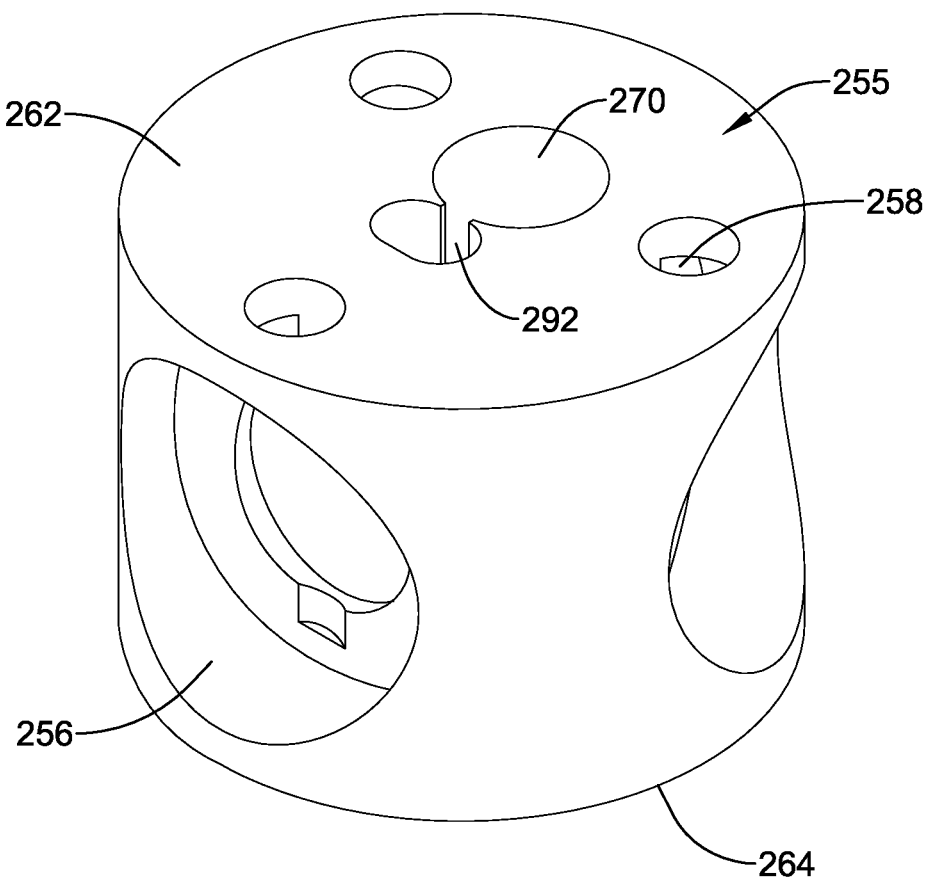
FIG. 8A is a top perspective view of the distal insert of FIG. 5.
Figure 8B:
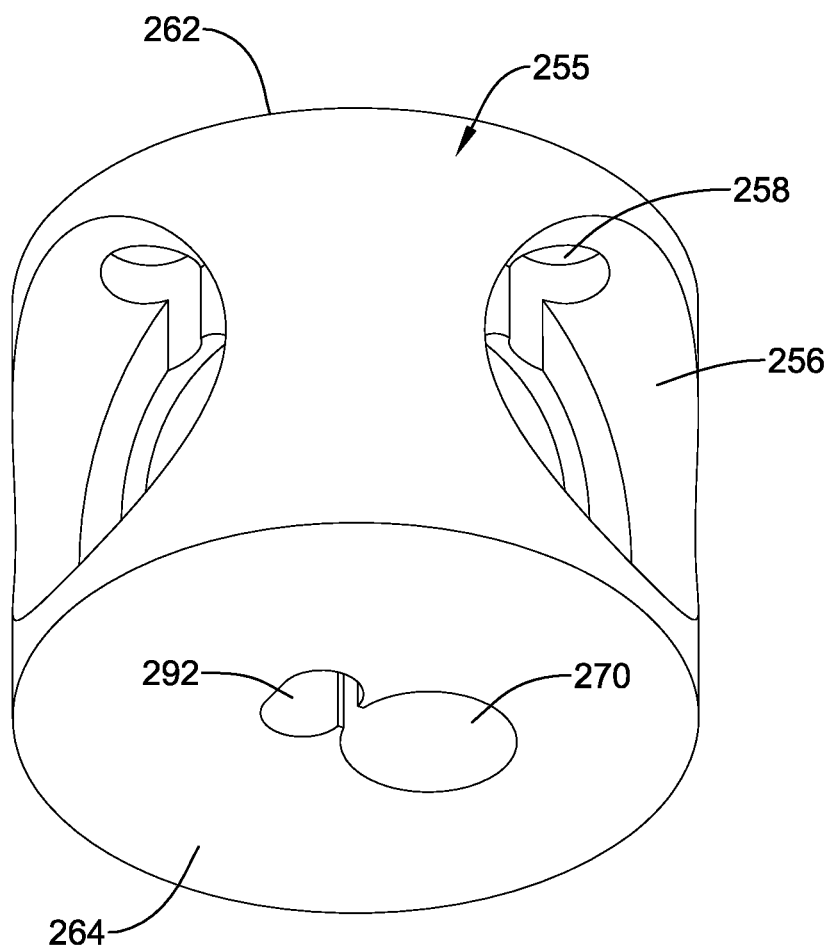
FIG. 8B is a bottom perspective view of the distal insert of FIG. 5.

Some cooling fluid may also flow directly through the lumen 282 and into the proximal fluid reservoir 265, where it may circulate before flowing into the lumen 270 in the distal insert 255 and into the distal fluid reservoir 260, where it may again circulate before flowing out through the irrigation ports 235, as shown by the fluid flow lines 25 in FIG. 5. A distal insert 255 divides the open interior region 230 of the electrode tip body 210 into a distal fluid reservoir 260 and a proximal fluid reservoir 265, each of which act as cooling chambers. The distal insert 255 may be a thermal mass. By way of example and not limitation, an embodiment of the distal insert is fabricated from stainless steel. As illustrated in FIGS. 8A and 8B, the distal insert 255 has an lumen 270 extending from a proximal surface 262 to a distal surface 264. The lumen 270 connects the distal fluid reservoir 260 and the proximal fluid reservoir 265. The distal insert 255 may include additional openings such as the opening 292 sized to receive a thermocouple.

The catheter system 200 may include one or more mapping electrodes 275, shown in phantom lines in the figures. The distal insert 255 illustrated in FIGS. 5, 8A, and 8B includes openings or apertures 256 sized to receive a mapping electrode 275. The electrode tip wall 225 has a corresponding opening 228 in an exterior surface 226 thereof. In one embodiment, the device includes three mapping electrodes 275 spaced equidistant around the electrode. Four our more mapping electrodes may also be used. The proximal surface 262 of the distal insert 255 may also include openings 258 sized to receive electrical conductors (not shown) used to provide electrical connections to the mapping electrodes 275. Electrical conduction for the mapping electrodes, the tip electrode, and the thermocouple may be incorporated into the catheter as generally known in the art.

Figure 9A:
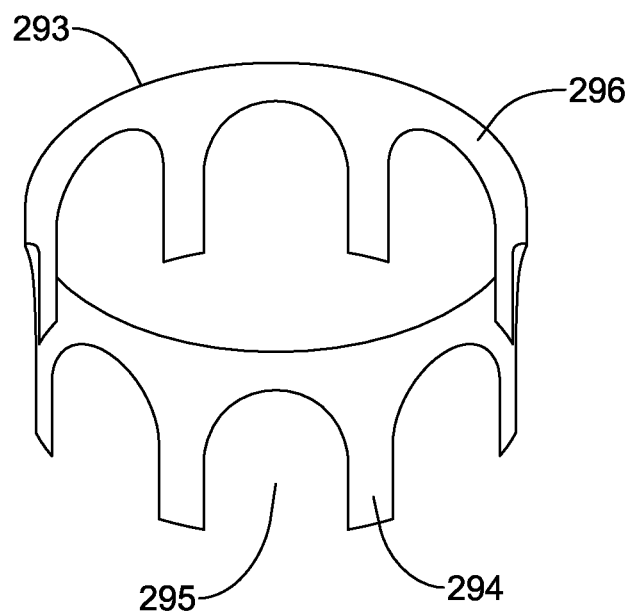
FIG. 9A is a perspective view of a crown according to an embodiment of the present subject matter.
Figure 9B:
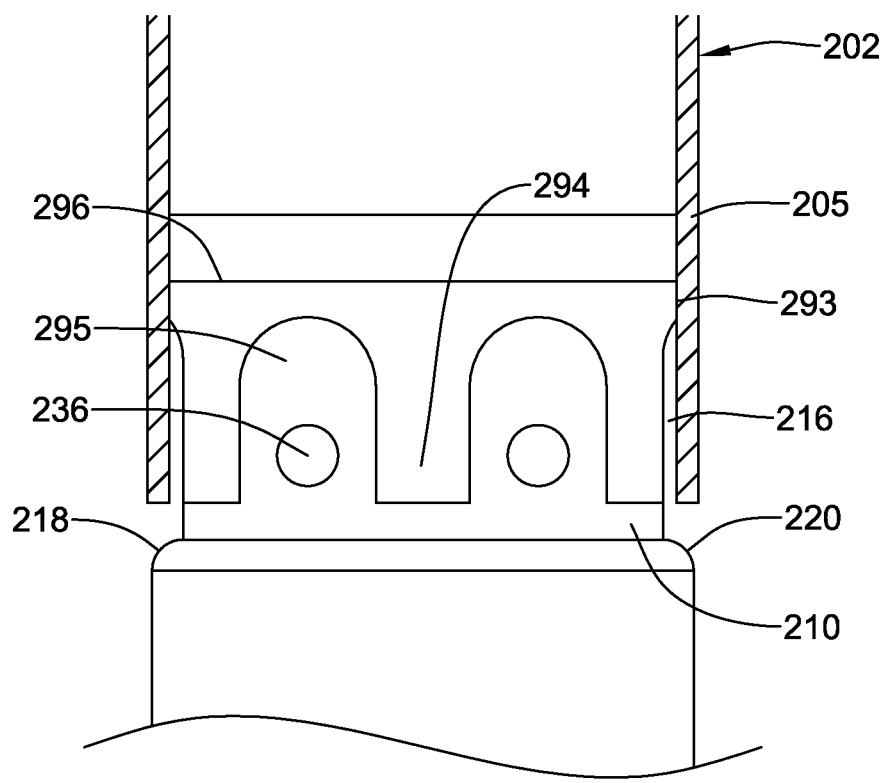
FIG. 9B is a side view of the electrode tip body of FIG. 5 with the crown of FIG. 9A.

In some embodiments, the catheter system 200 may include a crown 293 sized to fit over the proximal end 220 of the electrode tip body 210. As illustrated in FIG. 9A, the crown 293 includes one or more legs 294 separated by spaces 295. The legs 294 and spaces 295 are configured such that when the crown 293 is placed on the proximal end 220 of the electrode tip body, illustrated in FIG. 9B, the legs 294 extend in a distal direction and are disposed between the openings 236 in the electrode tip body. The crown 293 may have a lip 296 that engages the proximal edge of the electrode tip body and maintains the crown in position. The crown 293 has a thickness that blocks at least a portion of the space 216 between the catheter shaft 202 and the electrode tip body 210, thereby directing fluid flow from the openings 236, 285 distally toward the shoulder region 218 and out from under the distal-most edge of the catheter shaft 202.

Figure 10:
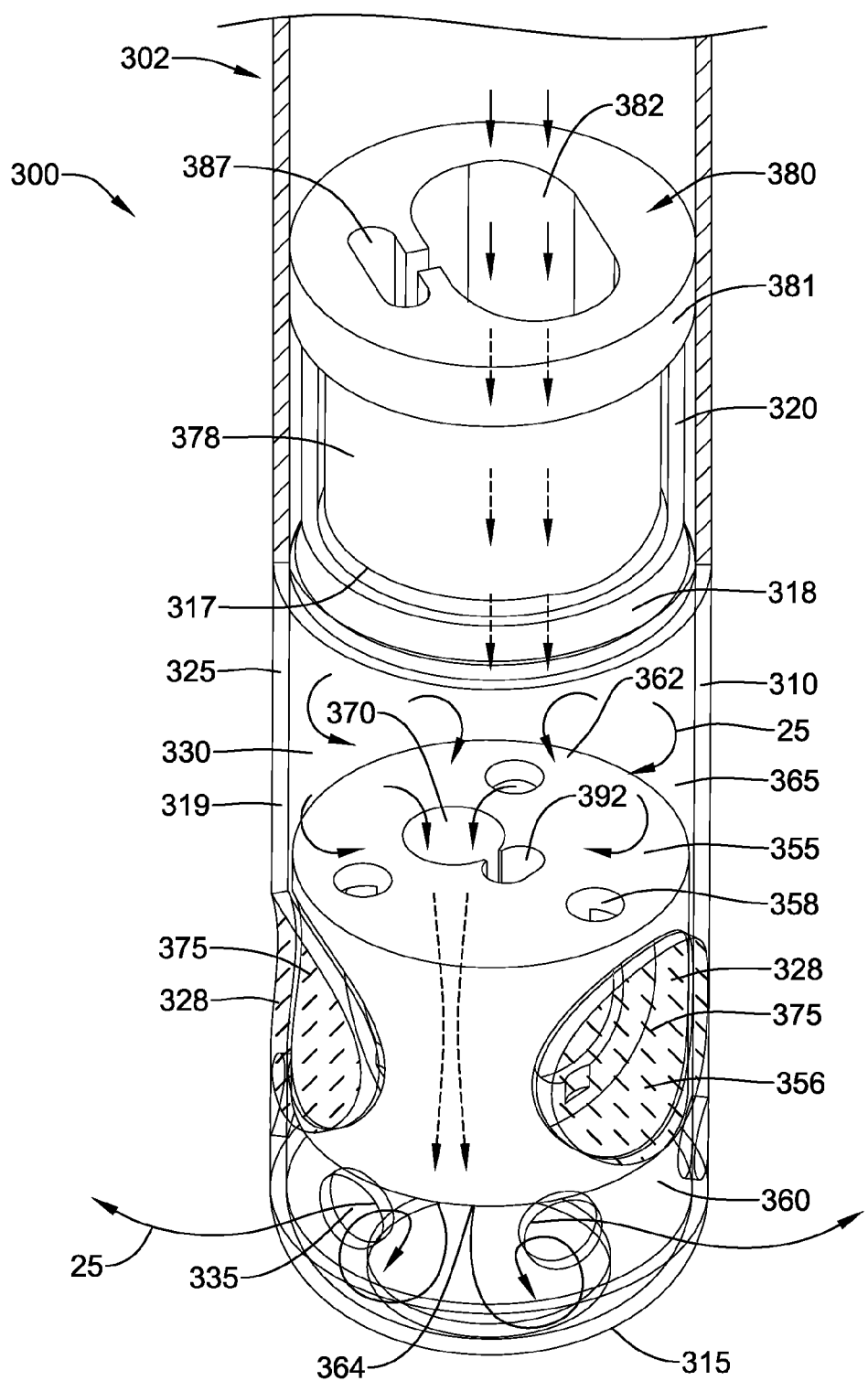
FIG. 10 is a perspective view of an open-irrigated catheter according to another embodiment of the present subject matter.
Figure 11:
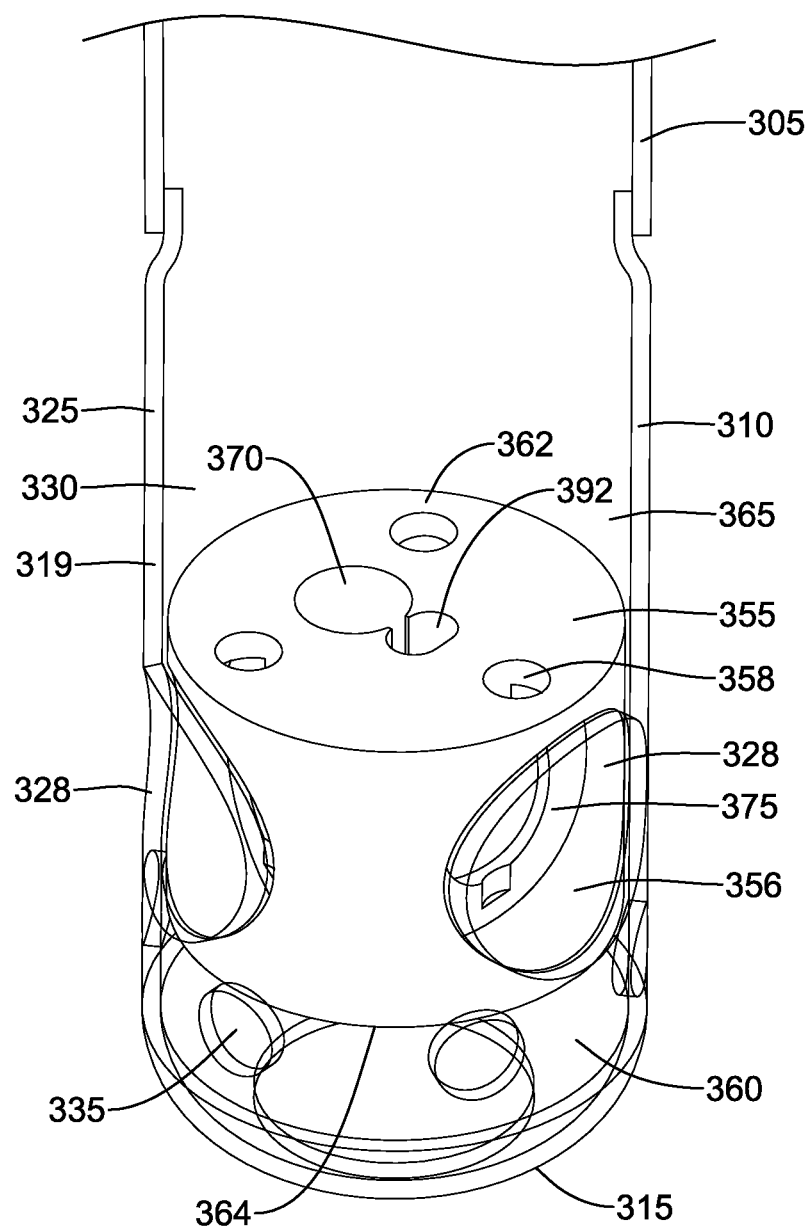
FIG. 11 is a side view of the open-irrigated catheter of FIG. 10.
Figure 12:
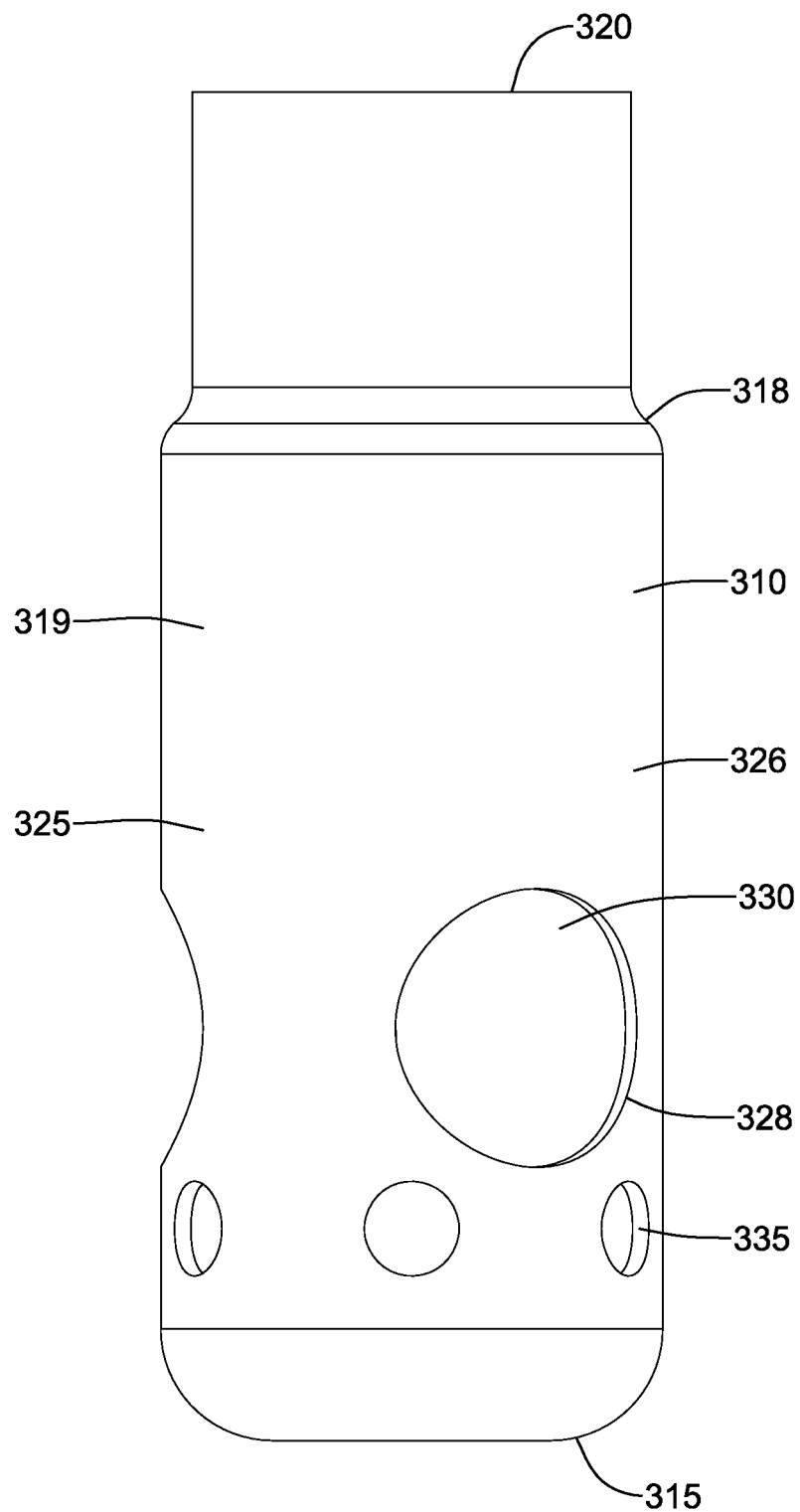
FIG. 12 is a side view of the electrode tip body of FIG. 10.

FIG. 10 illustrates the distal end of another open-irrigated catheter system 300 including an electrode tip body 310, a proximal insert 380, and a distal insert 355. The electrode tip body 310 shown in FIG. 10 is similar to that shown in FIG. 5, but without the openings 236. The electrode tip body 310 is generally hollow with a closed distal end 315, an open interior region 330, an open proximal end 320 and a main body 319. Referring to FIG. 12, the hollow electrode tip body 310 has a generally cylindrical shape with a planar distal end 315. The electrode tip body 310 may have a shoulder region 318 joining a smaller diameter proximal end 320 to the main body 319. The diameter of the main body 319 may be sized to correspond to a diameter of the distal end 305 of a catheter shaft 302, providing a flush join between the catheter shaft and the electrode tip body, as illustrated in FIG. 11.

The electrode tip body 310 may include one or more irrigation ports 335 through the wall 325 of the electrode tip body 310 near the distal end 315. When more than one irrigation port is present, the irrigation ports 335 may be spaced and arranged around the circumference of the electrode tip body in any manner and/or pattern. The electrode tip body 310 may also include one or more openings 328 for receiving electrodes such as mapping electrodes.

Referring to FIG. 10, a proximal insert 380 fits into the open proximal end 320 of the electrode tip body 310. The proximal insert 380 includes at least one fluid lumen 382 and may have a thermocouple opening 387 extending longitudinally therethrough. A proximal lip 381 may extend radially out from the main body 378 of the proximal insert 380. The main body 378 is sized to fit into the open proximal end 320 of the electrode tip body 310 with the proximal lip 381 resting on the proximal edge of the electrode tip body. An outer surface of the proximal lip 281 may be flush with an outer surface of the proximal end 320 of the electrode tip body, both of which fit within the distal end 305 of the catheter shaft 302. The proximal insert 380 has a length such that a distal end 317 of the proximal insert 380 resides proximal of the shoulder region 318. Cooling fluid, as shown by the fluid flow lines 25, exiting the distal end 317 of the proximal insert 380 cools the shoulder region 318 where the distal end 305 of the catheter shaft 302 meets the electrode tip body 310. The proximal insert may include a fluid diverting member to increase the circulation of fluid at the shoulder region 318 of the electrode tip body 310. For example, a plate 184 such as that illustrated in FIG. 1 may be attached to the proximal insert 380 or the electrode tip body 310.

A distal insert 355 divides the open interior region 330 of the electrode tip body 310 into a distal fluid reservoir 360 and a proximal fluid reservoir 365, each of which act as cooling chambers. The distal insert 355 may be a thermal mass. The distal insert 355 has an opening 370 extending from a proximal surface 362 to a distal surface 364. The opening 370 connects the distal fluid reservoir 360 and the proximal fluid reservoir 365. The distal insert 355 may include additional openings such as an opening 392 sized to receive a thermocouple (not shown).

The catheter system 300 may include one or more mapping electrodes 375. The distal insert 355 may include openings or apertures 356 sized to receive mapping electrodes 375. The electrode tip wall 325 has a corresponding opening 328 in an exterior surface 326 thereof. In one embodiment, the device includes three mapping electrodes 375 spaced equidistant around the electrode. Four our more mapping electrodes may also be used. The proximal surface 362 of the distal insert 355 may also include openings 358 sized to receive electrical conductors (not shown) used to provide electrical connections to the mapping electrodes 375. By way of example and not limitation, an embodiment of the distal insert is fabricated from stainless steel.

Figure 13:
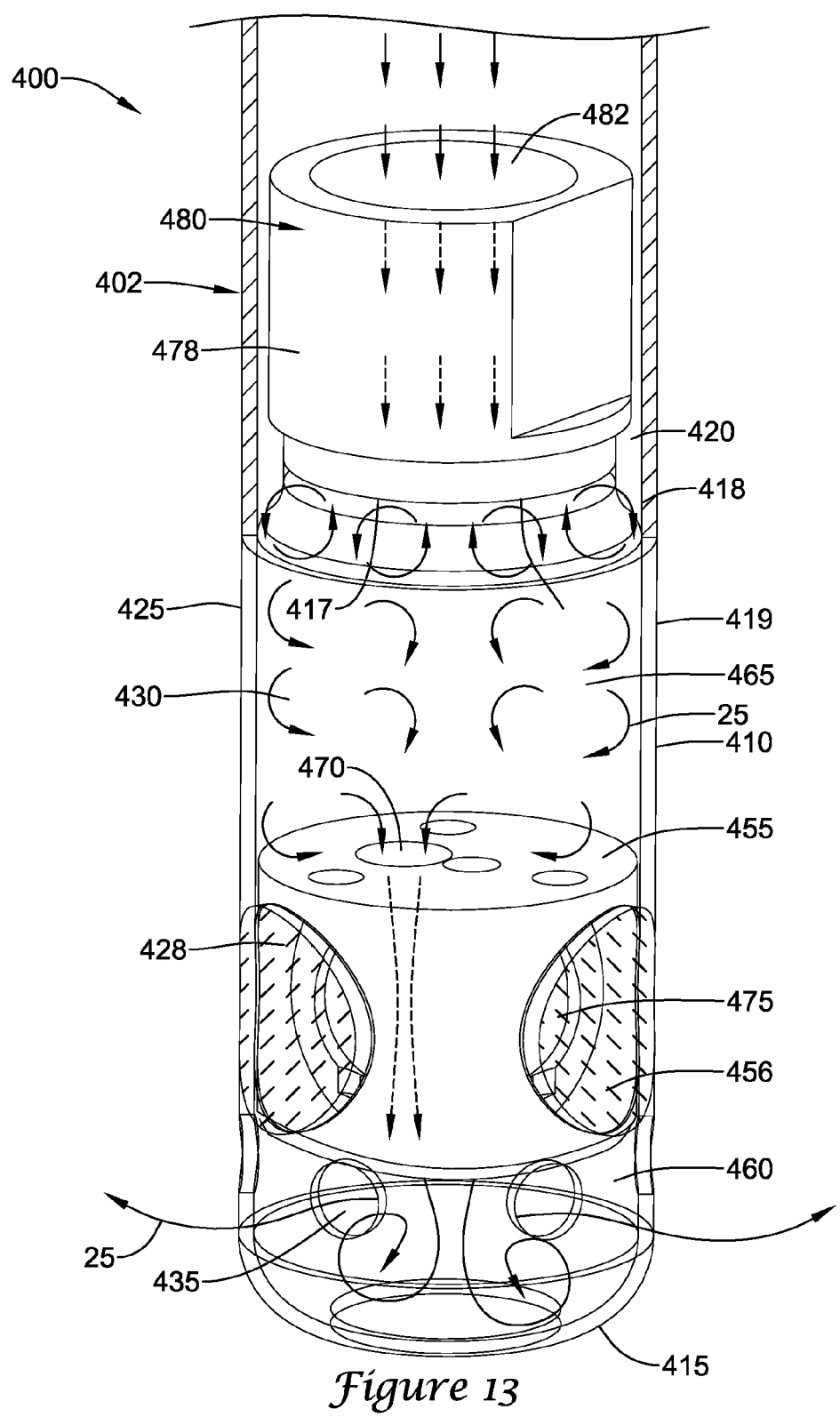
FIG. 13 is a perspective view of an open-irrigated catheter according to another embodiment of the present subject matter.
Figure 14:
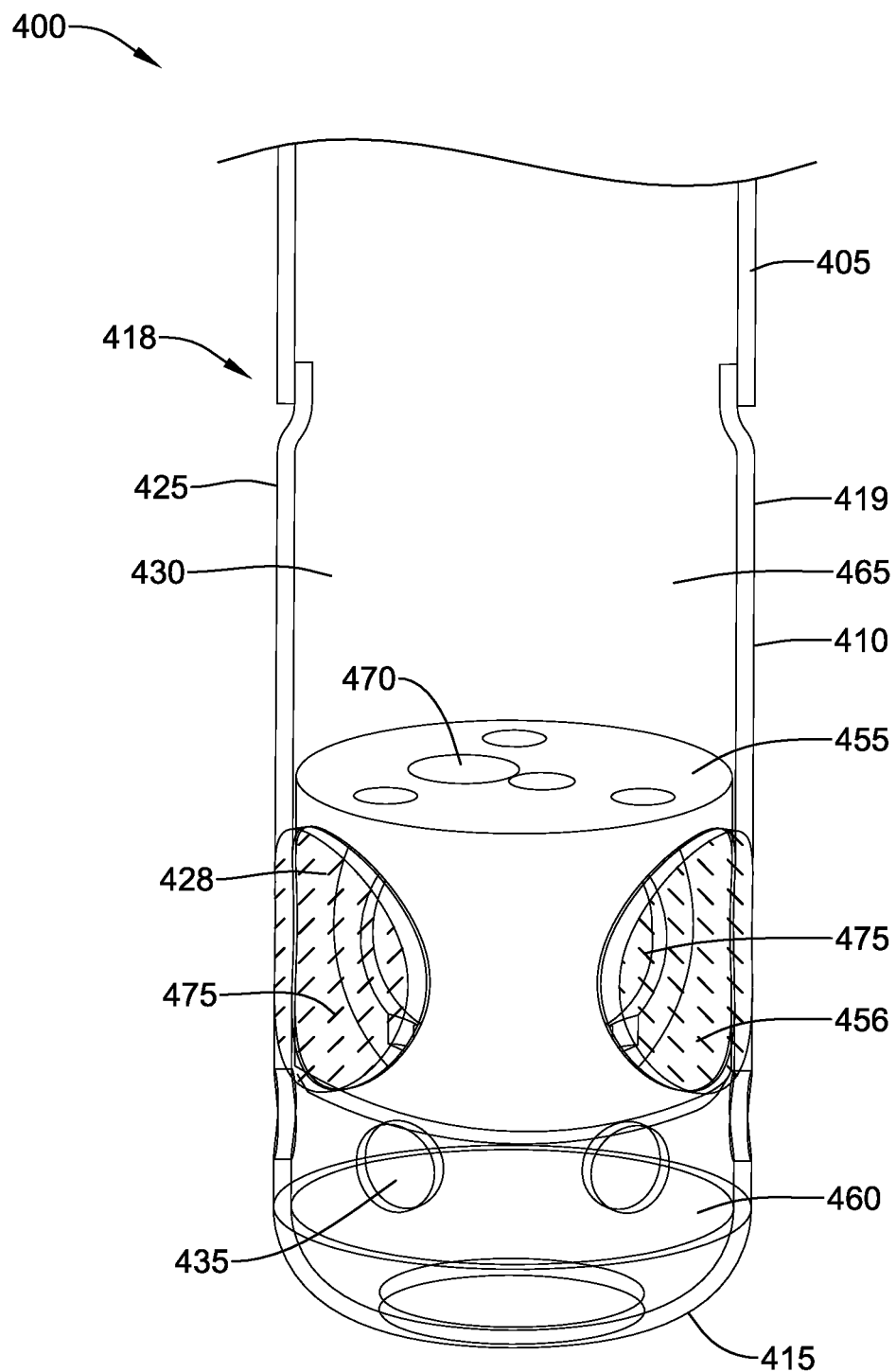
FIG. 14 is a side view of the open-irrigated catheter of FIG. 13.
Figure 15A:
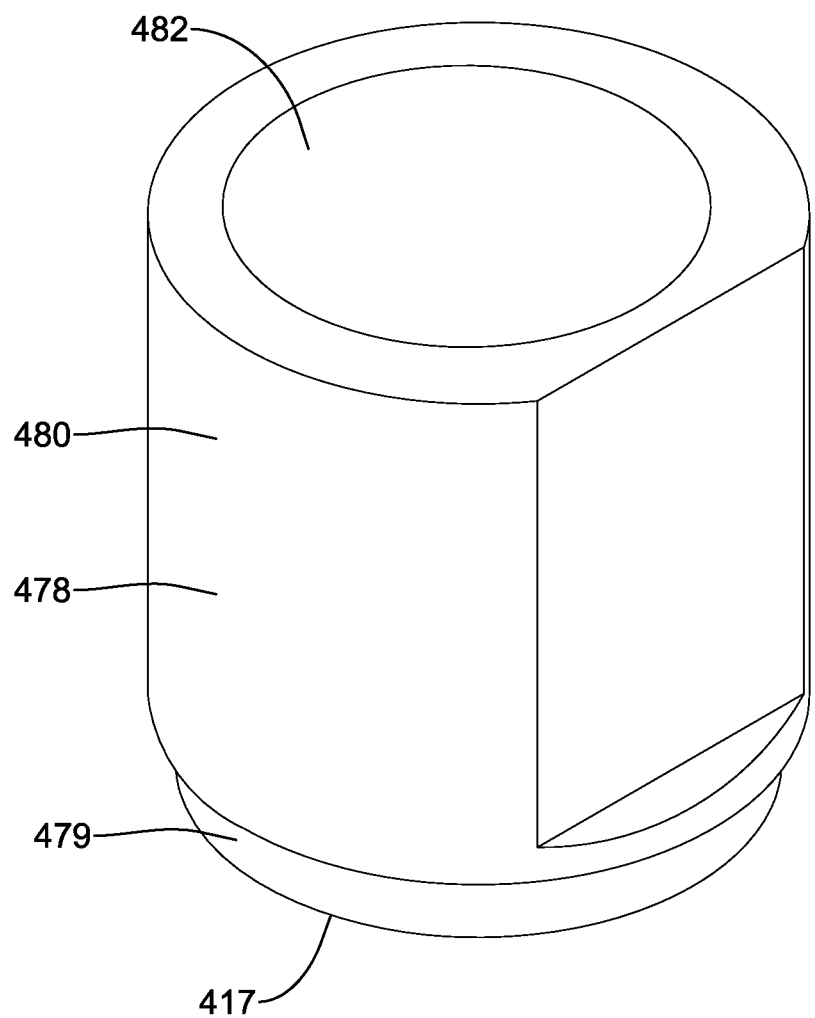
FIG. 15A is a perspective top view of the proximal insert of FIG. 13.
Figure 15B:
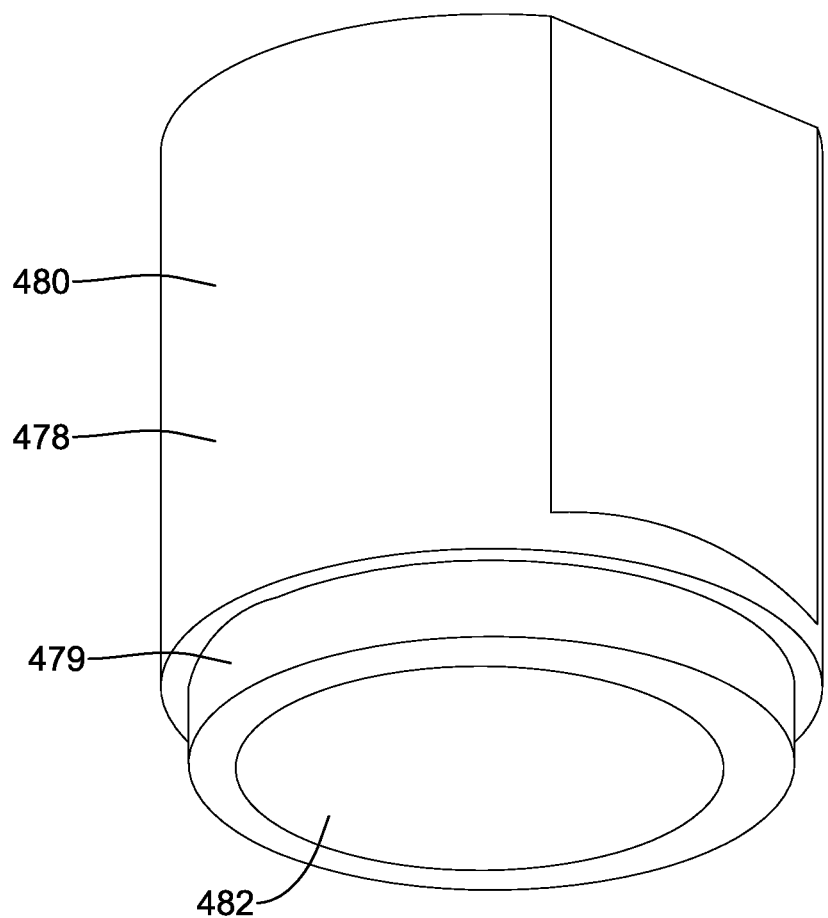
FIG. 15B is a perspective bottom view of the proximal insert of FIG. 13.
Figure 16:
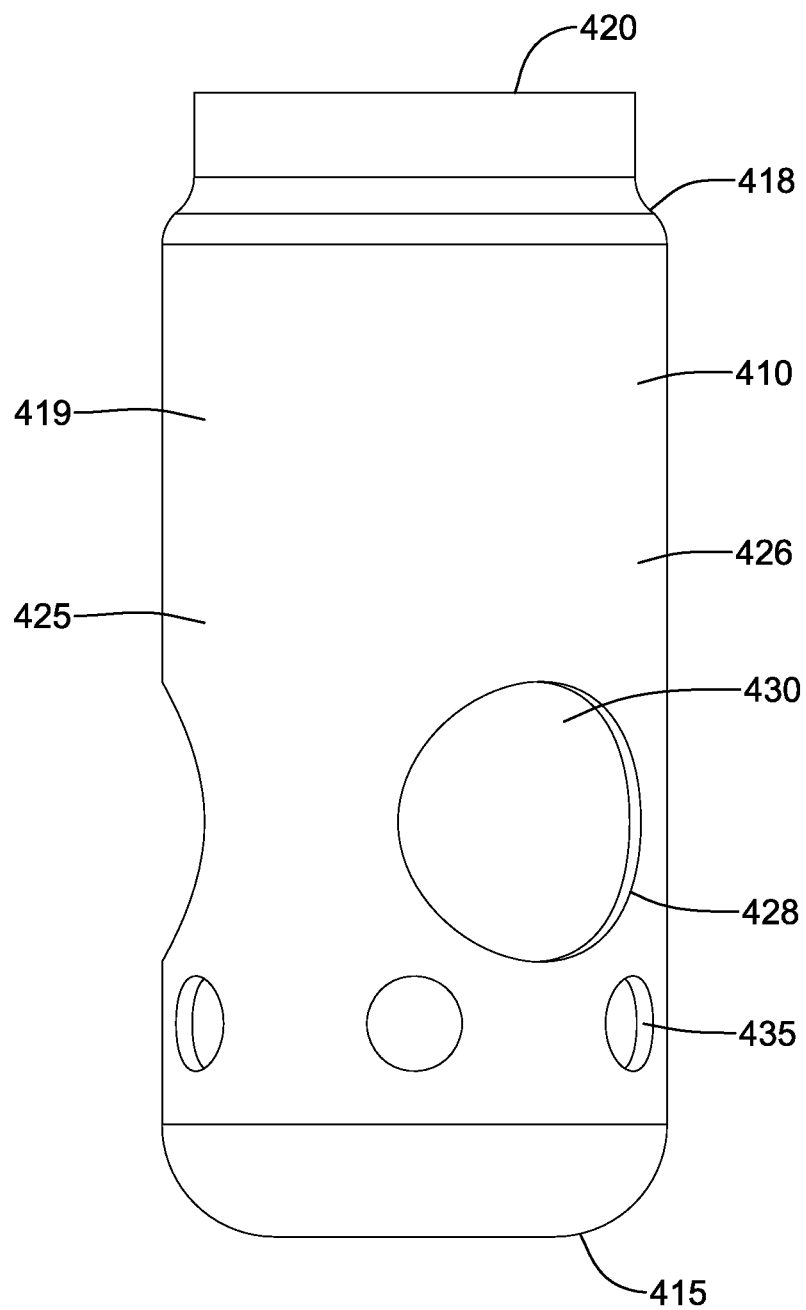
FIG. 16 is a side view of the electrode tip body of FIG. 13.
Figure 17A:
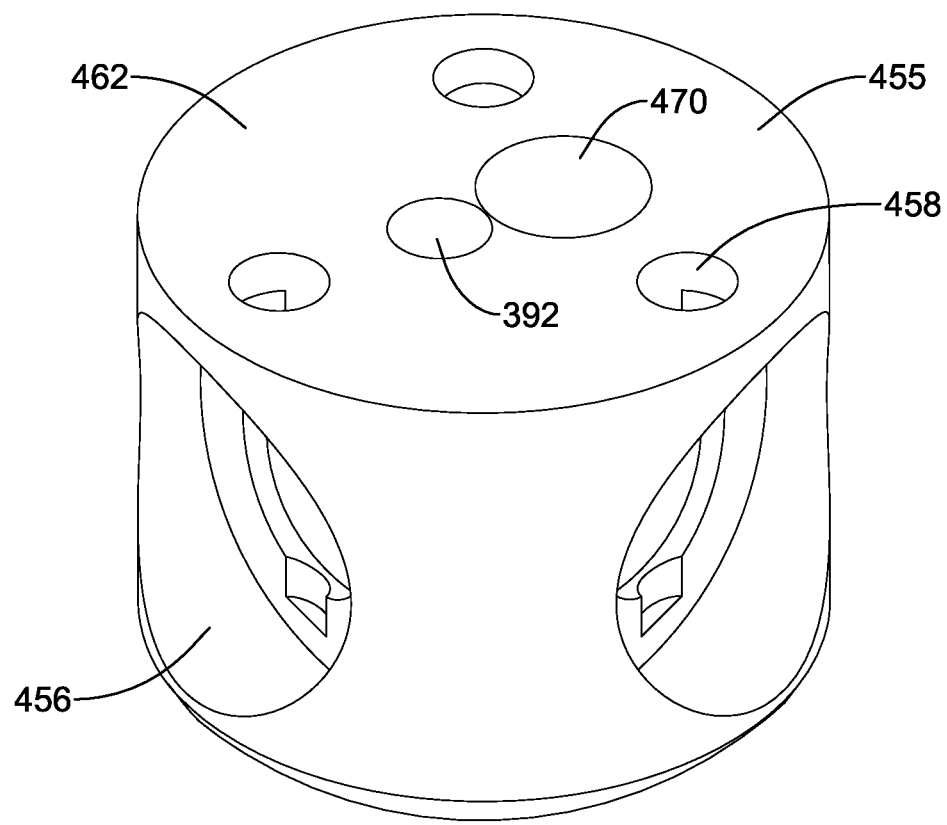
FIG. 17A is a top perspective view of the distal insert of FIG. 13.
Figure 17B:
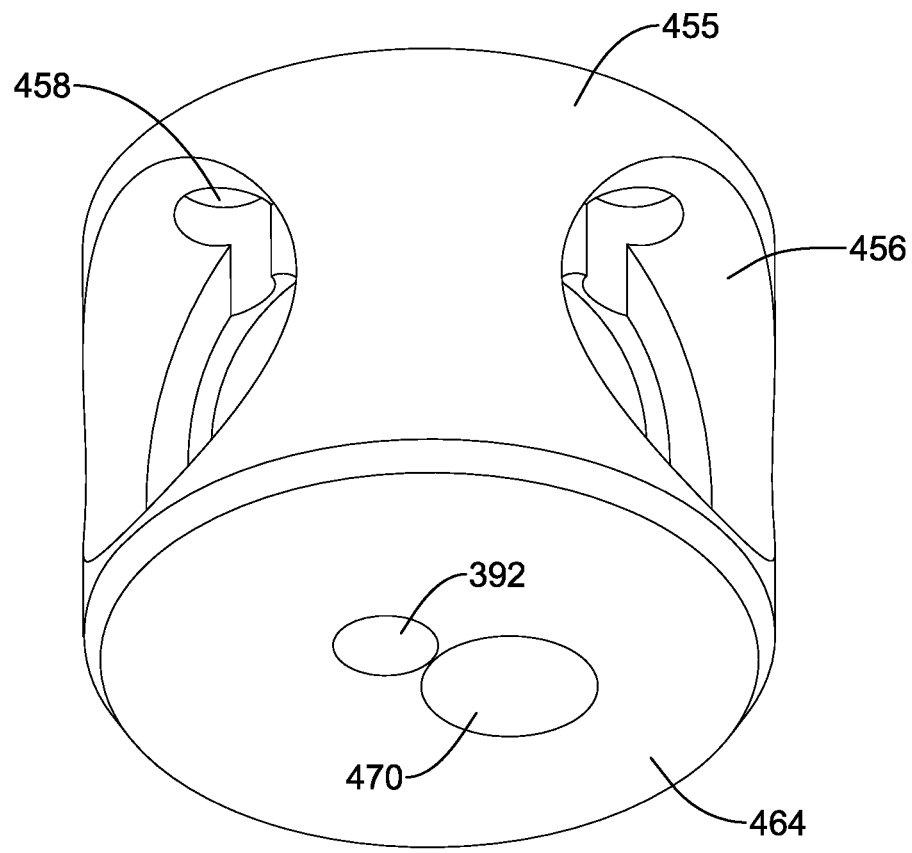
FIG. 17B is a bottom perspective view of the distal insert of FIG. 13.

FIG. 13 illustrates the distal end of another open-irrigated catheter system 400 including a catheter shaft 402, an electrode tip body 410, a proximal insert 480, and a distal insert 455. The electrode tip body 410 is generally hollow with a closed distal end 415, an open interior region 430, an open proximal end 420 and a main body 419. As illustrated in FIG. 16, the hollow electrode tip body 410 has a generally cylindrical shape with a planar distal end 415. The electrode tip body 410 may have a shoulder region 418 joining a smaller diameter proximal end 420 to the main body 419. The diameter of the main body 419 may be sized to correspond to a diameter of the distal end 405 of the catheter shaft 402, providing a flush join between the catheter shaft and the electrode tip body, as illustrated in FIG. 14.

The electrode tip body 410 may include one or more irrigation ports 435 through the wall 425 of the electrode tip body 410 near the distal end 415. When more than one irrigation port is present, the irrigation ports 435 may be spaced and arranged around the circumference of the electrode tip body in any manner and/or pattern. The electrode tip body 410 may also include one or more openings 428 for receiving electrodes such as mapping electrodes.

As seen in FIG. 13, a proximal insert 480 fits into the open proximal end 420 of the electrode tip body 410. The proximal insert 480 includes at least one fluid lumen 482 extending longitudinally therethrough. A distal reduced diameter region 479 of the proximal insert 480 is sized to fit into the open proximal end 420 of the electrode tip body 410 with the main body 478 of the proximal insert 480 resting on the proximal edge of the electrode tip body 410. An outer surface of the proximal insert main body 478 may be flush with an outer surface of the proximal end 420 of the electrode tip body, both of which fit within the distal end 405 of the catheter shaft 402. The proximal insert 480 has a length such that a distal end 417 of the proximal insert 480 resides proximal of the shoulder region 418. Cooling fluid, as shown by the fluid flow lines 25, exiting the distal end 417 of the proximal insert 480 cools the shoulder region 418 where the distal end 405 of the catheter shaft 402 meets the electrode tip body 410. The proximal insert may include a fluid diverting member to increase the circulation of fluid at the shoulder region 418 of the electrode tip body 410. For example, a plate 184 such as that illustrated in FIG. 1 may be attached to the proximal insert 480 or the electrode tip body 410.

A distal insert 455 divides the open interior region 430 of the electrode tip body 410 into a distal fluid reservoir 460 and a proximal fluid reservoir 465, each of which act as cooling chambers. The distal insert 455 may be a thermal mass. The distal insert 455 has an opening 470 extending from a proximal surface 462 to a distal surface 464. The opening 470 connects the distal fluid reservoir 460 and the proximal fluid reservoir 465. The distal insert 455 may include additional openings such as an opening 392 sized to receive a thermocouple (not shown).

The catheter system 400 may include one or more mapping electrodes 475. The distal insert 455 may include openings or apertures 456 sized to receive mapping electrodes 475. The electrode tip wall 425 has corresponding openings 428 in an exterior surface 426 thereof. In one embodiment, the device includes three mapping electrodes 475 spaced equidistant around the electrode. Four our more mapping electrodes may also be used. The proximal surface 462 of the distal insert 455 may also include openings 458 sized to receive electrical conductors (not shown) used to provide electrical connections to the mapping electrodes 375. By way of example and not limitation, an embodiment of the distal insert is fabricated from stainless steel.

By way of an example and not limitation, the electrode tip body may have a diameter on the order of about 0.08-0.1 inches (about 0.2032-0.254 cm), a length on the order of about 0.2-0.3 inches (about 0.508-0.762 cm), and an exterior wall with a thickness on the order of 0.003-0.004 inches (0.00762-0.01016 cm). The distal end may be planar. It should be noted that there are no holes in the distal end wall of the exemplary electrode tip body for fluid cooling and/or passage of a temperature sensor that is aligned with the outer surface of the electrode. Such holes would create regions of high current density and regions of high current density near the center of the electrode tip would work against efforts to move current to the outer perimeter of the electrode tip.

A plurality of irrigation ports 135, 235, 335, 435 or exit ports are shown near the distal end of the electrode tip body 110, 210, 310, 410 in FIGS. 1, 5, 10, and 13. By way of example and not limitation, an embodiment has irrigation ports with a diameter approximately within a range of 0.01 to 0.02 inches (0.0254 to 0.0508 cm). Fluid, such as a saline solution, flows from the distal fluid reservoir, through these ports to the exterior of the catheter. This fluid is used to cool the ablation electrode tip body and the tissue near the electrode. This temperature control reduces coagulum formation on the tip of the catheter, prevents impedance rise of tissue in contact with the catheter tip, and increases energy transfer to the tissue because of the lower tissue impedance.

With respect to material, the exemplary electrode tip bodies may be formed from any suitable electrically conductive material. By way of example, but not limitation, suitable materials for the main portion of the electrode tip body, i.e. the side wall and planar distal end, include silver, platinum, gold, stainless steel, plated brass, platinum iridium and combinations thereof. For example, some embodiments use a platinum-iridium alloy. Some embodiments use an alloy with approximately 90% platinum and 10% iridium. This conductive material is used to conduct RF energy used to form legions during the ablation procedure. In embodiments of the electrode tip having a main body region with a larger diameter than a proximal region with a shoulder region therebetween, the reduction in diameter may be achieved by swaging. Alternatively, separate pieces of differing diameter may be laser welded or soldered together to form the electrode tip body.

The distal insert may be a thermal mass formed from any suitable electrically and thermally conducting material such as, for example, brass, copper and stainless. The distal insert may, alternatively, be made of thermally conducting and electrically non-conducing materials.

The proximal insert may be mounted within the proximal region of the electrode tip body. The proximal insert may be formed from an electrically conductive material such as stainless steel, or an electrically non-conductive material such as nylon or polyimide. The proximal insert may include any number of lumens for fluid flow and for receiving a thermocouple, steering element, electrical conductor, or other element. Alternatively, a fluid conduit may be placed within one of the lumens. A steering center support may be positioned within a lumen and be secured to the proximal insert.

The catheter systems 100, 200, 300, 400 are part of a mapping and ablation system that includes an open-irrigated catheter. The systems 100, 200, 300, 400 include an ablation electrode tip body 110, 210, 310, 410 with mapping electrodes 175 and irrigation ports 135, 235, 335, 435. The catheter may be functionally divided into four regions: the operative distal probe assembly region (e.g. the distal portion of catheter shaft 102, 202, 302, 402), a main catheter region (not shown), a deflectable catheter region (not shown), and a proximal catheter handle region (not shown) where a handle assembly (not shown) is attached. The catheter body includes a coolant flow path or conduit and may include other tubular element(s) to provide the desired functionality to the catheter. The addition of metal in the form of a braided mesh layer (not shown) sandwiched in between layers of plastic tubing may be used to increase the rotational stiffness of the catheter.

A deflectable catheter region allows the catheter to be steered through the vasculature of the patient and allows the probe assembly to be accurately placed adjacent the targeted tissue region. A steering wire (not shown) may be slidably disposed within the catheter body. A handle assembly (not shown) may include a steering member such as a rotating steering knob that is rotatably mounted to the handle. Rotational movement of the steering knob relative to the handle in a first direction may cause a steering wire to move proximally relative to the catheter body which, in turn, tensions the steering wire, thus pulling and bending the catheter deflectable region into an arc; and rotational movement of the steering knob relative to the handle in a second direction may cause the steering wire to move distally relative to the catheter body which, in turn, relaxes the steering wire, thus allowing the catheter to return toward its form. To assist in the deflection of the catheter, the deflectable catheter region may be made of a lower durometer plastic than the main catheter region.

The system may include an RF generator (not shown) used to generate the energy for the ablation procedure. An RF generator may include a source for the RF energy and a controller for controlling the timing and the level of the RF energy delivered through the electrode tip body. The system may include a fluid reservoir and pump (not shown) for pumping cooling fluid, such as a saline, through the catheter and out through the irrigation ports. A mapping signal processor (not shown) may be connected to the mapping electrodes. The mapping signal processor and mapping electrodes detect electrical activity of the heart. This electrical activity is evaluated to analyze an arrhythmia and to determine where to deliver the ablation energy as a therapy for the arrhythmia. One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method. Additional details concerning this type of catheter system may be found in, for example, U.S. Publication. Nos. 2008/0243214, 2009/0093810, 2010/0331658, and 2011/0009857, which are hereby incorporated by reference.

With respect to steering, the exemplary catheter systems 100, 200, 300 400 illustrated in FIGS. 1, 5, 10, and 13 may be provided with a conventional steering mechanism. For example, the catheter may include a steering wire (not shown) slidably disposed within the catheter body, or a steering center support and steering wire arrangement (not shown). A steering center support with a pair of adjacent steering wires may extend through the catheter body to a handle (not shown), which is also configured for steering. Additional details concerning this type of steering arrangement may be found in, for example, U.S. Pat. Nos. 5,871,525 and 6,287,301, which are hereby incorporated by reference. Other suitable steering arrangements are disclosed in U.S. Pat. Nos. 6,013,052 and 6,287,301, which are hereby incorporated by reference. Nevertheless, it should be noted that the present inventions are not limited to steerable catheter apparatus, or to any particular type of steering arrangement in those catheter apparatus which are steerable.

The materials that can be used for the various components of the open-irrigated ablation catheters disclosed herein may vary. For simplicity purposes, the following discussion makes reference to the catheter body. However, this is not intended to limit the devices and methods described herein, as the discussion may be applied to other similar tubular members and/or components of tubular members or devices disclosed herein. The various components of the system, such as the electrode tip, proximal insert, and fluid diverting member may be a single monolithic structure or separate elements.

Catheter body and/or other components of catheter system may be made from a metal, metal alloy, polymer (some examples of which are disclosed below), a shape memory polymer, a metal-polymer composite, ceramics, other composites, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties. Shape memory polymer materials may also be used for catheter body.

In at least some embodiments, portions or all of catheter body may also be loaded with, made of, or otherwise include a radiopaque material. Radiopaque materials are understood to be materials capable of producing a relatively bright image on a fluoroscopy screen or another imaging technique during a medical procedure. This relatively bright image aids the user of catheter system in determining its location. Some examples of radiopaque materials can include, but are not limited to, gold, platinum, palladium, tantalum, tungsten alloy, polymer material loaded with a radiopaque filler (e.g., barium sulfate, bismuth subcarbonate, etc.), and the like. Additionally, other radiopaque marker bands and/or coils may also be incorporated into the design of catheter system 100 to achieve the same result.

In some embodiments, a degree of Magnetic Resonance Imaging (MRI) compatibility is imparted into catheter system. For example, catheter body, or portions thereof, may be made of a material that does not substantially distort the image and create substantial artifacts (i.e., gaps in the image). Certain ferromagnetic materials, for example, may not be suitable because they may create artifacts in an MRI image. The catheter body, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of the catheter body that may define a generally smooth outer surface for the catheter system. In other embodiments, however, such a sheath or covering may be absent from a portion of all of the catheter system. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the catheter system may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portions of the catheter system. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An open-irrigated ablation catheter system, comprising:
a catheter body;
an electrode tip body having a distal end and a proximal end, the proximal end configured for connection to the catheter body, the electrode tip body having a central longitudinal axis and a wall defining an open interior region, the wall having one or more irrigation ports in fluid communication with the open interior region, wherein the wall is conductive for delivering radio frequency (RF) energy;
a proximal insert positioned at least partially within the proximal end of the electrode tip body, the proximal insert defining at least one lumen extending therethrough; and
a fluid diverting member spaced from a distal end of the lumen and attached to the wall by a plurality of legs extending between the wall and the proximal insert, the plurality of legs defining a plurality of openings, the fluid diverting member extending across at least a portion of the lumen such that at least a portion of fluid flowing distally through the lumen impacts the fluid diverting member and is diverted radially outward through the plurality of openings from the central longitudinal axis towards the wall before flowing into the interior region and out through the one or more irrigation ports.

2. The catheter system of claim 1, wherein the fluid diverting member extends across the entire lumen such that all fluid flowing distally through the lumen impacts the fluid diverting member and is diverted towards the wall.

3. The catheter system of claim 1, wherein the fluid diverting member is sized relative to the electrode tip body to achieve a predetermined circulation of fluid between the distal end of the lumen and the fluid diverting member.

4. The catheter system of claim 1, further comprising a distal insert positioned within the electrode tip body, the distal insert separating the open interior region into a distal fluid chamber and a proximal fluid chamber, the distal insert having an opening fluidly connecting the distal and proximal fluid chambers, wherein at least one of the irrigation ports is in fluid communication with the distal fluid chamber, and wherein the fluid diverting member is positioned in the proximal fluid chamber.

5. The catheter system of claim 1, further comprising one or more mapping electrodes.

6. The catheter system of claim 1, further comprising a thermocouple, wherein the fluid diverting member defines a thermocouple opening extending therethrough, wherein the thermocouple is disposed through the thermocouple opening with a distal end of the thermocouple disposed adjacent the distal end of the electrode tip body.

7. The catheter system of claim 1, wherein the distal end of the electrode tip body is closed and the proximal end of the electrode tip body is open.

8. The catheter system of claim 1, wherein a surface of the fluid diverting member facing the lumen is angled relative to the central longitudinal axis.

9. An open-irrigated ablation catheter system, comprising:
a catheter body;
an electrode tip body with a distal end and a proximal end configured for connection to the catheter body, the electrode tip body having a wall defining an open interior region, the electrode tip body including a main body portion and a proximal portion, the main body portion having one or more irrigation port in fluid communication with the open interior region, the proximal portion having one or more openings through the wall, wherein the wall is conductive for delivering radio frequency (RF) energy; and
a proximal insert positioned at least partially within the proximal end of the electrode tip body, the proximal insert including a proximal lip and a main body portion, wherein the main body portion has a diameter less than a diameter of the proximal lip, the proximal insert including at least one lumen extending therethrough, the proximal insert including one or more openings through a sidewall in the main body portion in fluid communication with the at least one lumen;

wherein the main body portion of the proximal insert is sized to be mounted within the proximal portion of the electrode tip body with the proximal lip extending radially beyond the electrode tip body, substantially aligning the openings in the proximal insert and the openings in the proximal portion of the electrode tip body, wherein the proximal lip is sized to engage an inner surface of a distal portion of the catheter body and define a space between an outer surface of the proximal portion of the electrode tip body and the inner surface of the catheter body such that a portion of cooling fluid flowing through the at least one lumen passes through the openings in the proximal insert and the openings in the proximal portion of the electrode tip body and into the space between the catheter body and the electrode tip body, thereby cooling a region where the catheter body joins the electrode tip body.

10. The catheter system of claim 9, wherein the proximal portion of the electrode tip body has a smaller diameter than the main body portion, with a shoulder region joining the proximal and main body portions, wherein a distal end of the catheter body is adjacent the shoulder region, allowing fluid passing through the openings in the proximal insert and the openings in the proximal portion of the electrode tip body to circulate in the space before passing through a gap between the distal end of the catheter body and the electrode tip body.

11. The catheter system of claim 9, wherein a distal end of the at least one lumen is proximal of the shoulder region.

12. The catheter system of claim 9, further comprising a distal insert positioned within the electrode tip body to separate the open interior region into a distal fluid chamber and a proximal fluid chamber, the distal insert having an opening fluidly connecting the distal and proximal fluid chambers, wherein at least one of the irrigation ports is in fluid communication with the distal fluid chamber.

13. The catheter system of claim 12, further comprising a thermocouple, wherein the at least one lumen includes a lumen sized to receive the thermocouple and the distal insert includes an opening sized to receive the thermocouple, wherein the thermocouple extends through the proximal and distal inserts such that a distal end of the thermocouple is disposed adjacent the closed distal end of the electrode tip body.

14. The catheter system of claim 9, further comprising one or more mapping electrodes.

15. The catheter system of claim 14, wherein the distal insert includes one or more openings therein sized to receive the one or more mapping electrodes.

16. The catheter system of claim 9, further comprising a crown element configured to fit over the proximal end of the electrode tip body, the crown element having one or more spaced apart legs, wherein the legs are configured to be disposed between the openings through the wall of the proximal portion of the electrode tip body, the crown directing fluid flow from the openings in the proximal portion toward the distal end of the catheter body.

17. The catheter system of claim 16, wherein the crown element has a thickness such that the crown element fills the space between the catheter body and the proximal portion of the electrode tip body.

18. An open-irrigated ablation catheter system, comprising:
a catheter body;
an electrode tip body having a distal end and a proximal end configured for connection to the catheter body, the electrode tip body having a central longitudinal axis and a wall defining an open interior region, the wall having one or more irrigation ports in fluid communication with the open interior region, wherein the wall is conductive for delivering radio frequency energy;
a proximal insert positioned at the proximal end of the electrode tip body, the proximal insert having a main body and a lip extending radially from the main body to couple the main body to the electrode tip body, wherein the main body has a diameter less than a diameter of the lip, and wherein the lip is positioned at a distal end of the proximal insert, the proximal insert defining at least one lumen extending therethrough; and
a fluid diverting member spaced from a distal end of the lumen, the fluid diverting member extending across at least a portion of the lumen such that at least a portion of fluid flowing distally through the lumen impacts the fluid diverting member and is diverted radially outward from the central longitudinal axis towards the wall before flowing into the interior region and out through the one or more irrigation ports.

* * * * *